(12) United States Patent
Itkowitz et al.

(10) Patent No.: US 8,543,240 B2
(45) Date of Patent: Sep. 24, 2013

(54) MASTER FINGER TRACKING DEVICE AND METHOD OF USE IN A MINIMALLY INVASIVE SURGICAL SYSTEM

(75) Inventors: Brandon D. Itkowitz, Sunnyvale, CA (US); Simon P. DiMaio, Sunnyvale, CA (US); Karlin Y. Bark, Philadelphia, PA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 305 days.

(21) Appl. No.: 12/887,254

(22) Filed: Sep. 21, 2010

(65) Prior Publication Data

US 2011/0118753 A1 May 19, 2011

Related U.S. Application Data

(63) Continuation-in-part of application No. 12/617,937, filed on Nov. 13, 2009.

(51) Int. Cl.
*G01N 27/416* (2006.01)

(52) U.S. Cl.
USPC ....... 700/258; 414/2; 414/7; 446/26; 601/130

(58) Field of Classification Search
USPC .................. 606/1, 130, 190, 142; 227/180.1; 706/14; 700/245, 258; 395/99; 414/5, 7, 414/2; 601/130; 446/26
See application file for complete search history.

(56) References Cited

U.S. PATENT DOCUMENTS

| 5,599,151 | A |   | 2/1997 | Daum et al. |
|---|---|---|---|---|
| 5,813,813 | A | * | 9/1998 | Daum et al. ................. 414/7 |
| 6,126,373 | A | * | 10/2000 | Yee et al. ..................... 414/5 |
| 6,331,181 | B1 |   | 12/2001 | Tierney et al. |
| 6,965,812 | B2 | * | 11/2005 | Wang et al. ............... 700/258 |
| 7,155,315 | B2 |   | 12/2006 | Niemeyer et al. |
| 7,395,249 | B2 | * | 7/2008 | Wang et al. ............... 706/14 |
| 7,574,250 | B2 |   | 8/2009 | Niemeyer |
| 7,695,481 | B2 | * | 4/2010 | Wang et al. ............... 606/130 |

(Continued)

FOREIGN PATENT DOCUMENTS

| EP | 1716802 A1 | 11/2006 |
|---|---|---|
| WO | WO9851451 A2 | 11/1998 |
| WO | WO9921478 A1 | 5/1999 |

OTHER PUBLICATIONS

Coogan, Thomas et al., "Real Time Hand Gesture Recognition Including Hand Segmentation and Tracking," ISVC 2006, 2nd International Symposium on Visual Computing, Lake Tahoe, NV, Nov. 6-8, 2006, 10 pages, Dublin City University, Dublin, Ireland.

(Continued)

*Primary Examiner* — Ronnie Mancho

(57) ABSTRACT

In a minimally invasive surgical system, a hand tracking system tracks a location of a sensor element mounted on part of a human hand. A system control parameter is generated based on the location of the part of the human hand. Operation of the minimally invasive surgical system is controlled using the system control parameter. Thus, the minimally invasive surgical system includes a hand tracking system. The hand tracking system tracks a location of part of a human hand. A controller coupled to the hand tracking system converts the location to a system control parameter, and injects into the minimally invasive surgical system a command based on the system control parameter.

18 Claims, 18 Drawing Sheets

(56) References Cited

U.S. PATENT DOCUMENTS

| | | | |
|---|---|---|---|
| 7,914,521 B2* | 3/2011 | Wang et al. | 606/1 |
| 7,976,559 B2* | 7/2011 | Goldfarb et al. | 606/190 |
| 8,172,124 B2* | 5/2012 | Shelton et al. | 227/180.1 |
| 8,236,010 B2* | 8/2012 | Ortiz et al. | 606/142 |
| 2002/0130673 A1 | 9/2002 | Pelrine et al. | |
| 2004/0236541 A1 | 11/2004 | Kramer et al. | |
| 2007/0156017 A1 | 7/2007 | Lamprecht et al. | |
| 2007/0167702 A1 | 7/2007 | Hasser et al. | |
| 2008/0046122 A1 | 2/2008 | Manzo et al. | |
| 2008/0065105 A1 | 3/2008 | Larkin et al. | |
| 2009/0036902 A1 | 2/2009 | DiMaio et al. | |
| 2009/0138025 A1 | 5/2009 | Stahler et al. | |
| 2009/0192523 A1 | 7/2009 | Larkin et al. | |
| 2010/0164950 A1 | 7/2010 | Zhao et al. | |
| 2010/0317965 A1 | 12/2010 | Itkowitz et al. | |
| 2010/0318099 A1 | 12/2010 | Itkowitz et al. | |

OTHER PUBLICATIONS

U.S. Appl. No. 12/780,568, filed May 14, 2010.
U.S. Appl. No. 12/887,091, filed Sep. 21, 2010.
U.S. Appl. No. 12/886,993, filed Sep. 21, 2010.
U.S. Appl. No. 12/887,160, filed Sep. 21, 2010.
Crabb, Ryan et al., "Real-time Foreground Segmentation via Range and Color Imaging," Proceedings IEEE Conference on Computer Vision and Pattern Recognition, Workshop on Time of Flight Camera Based Computer Vision, 2008, 5 pages, CA, USA.
Finger, Jonathan et al., "Video Matting from Depth Maps," 2007, 5 pages, University of California Santa Cruz, Santa Cruz, CA, USA.
Garg, Pragati et al., "Vision Based Hand Gesture Recognition," World Academy of Science, Engineering and Technology, Jan. 2009, pp. 972-977, Issue 49.
Götürk, Salih Burak et al., "3D Head Tracking Based on Recognition and Interpolation Using a Time-of-Flight Depth Sensor," 2004, 7 pages.
Guizzo, Erico , "Humanoid Robot Mahru Mimics a Person's Movements in Real Time," Blogs // Automaton, posted Apr. 27, 2010, IEEE Spectrum, 3 pages; Internet: http://spectrum.ieee.org/automaton/robotics/humanoids/042710-humanoid-robot-mahru-real-time-teleoperation.
Guthrie, Bart, "Virtual Interactive Surgery," UAB Insight on Neurosciences: Neurology and Neurosurgery magazine, Spring 2010, vol. 2, No. 2, p. 6; published by UAB Health System, Birmingham, Alabama.
Hardesty, Larry, "Gesture-based computing on the cheap," MIT news, Posted May 20, 2010, 5 pages; Internet: http://web.mit.edu/newsoffice/2010/gesture-computing-0520.html.
Itkowitz, Brandon, "Pen-Based 3D Trajectory Gesture Recognition," PowerPoint Presentation, Department of Electrical and Computer Engineering, Boston University, Dec. 2006, 19 pages.
Itkowitz, Brandon, "Pen-Based 3D Trajectory Gesture Recognition," Text Version, Department of Electrical and Computer Engineering, Boston University, Dec. 2006, 6 pages.
Kim, In-Cheol and Sung-Il Chien, "Analysis of 3D Hand Trajectory Gestures Using Stroke-Based Composite Hidden Markov Models," Applied Intelligence, vol. 15, No. 2, Sep.-Oct. 2001, pp. 131-143.
Liu, Nianjun et al., "Effect of Initial HMM Choices in Multiple Sequence Training for Gesture Recognition," International Conference on Information Technology: Coding and Computing (ITCC 04), Apr. 5-7, 2004, Las Vegas, Nevada, vol. 1, pp. 608-613.
Lockton, Ray, "Hand Gesture Recognition Using Computer Vision," 4th Year Project Report, 2002, pp. 1-69, Oxford University, Oxford, UK.
Moghaddam, Baback and Alex Pentland, "Probabilistic Visual Learning for Object Detection," MIT Media laboratory Perceptual Computing Section Technical Report No. 326, 5th International Conference on Computer Vision, Cambridge, MA, Jun. 1995, 8 pages.
Moghaddam, Baback and Alex Pentland, "Probabilistic Visual Learning for Object Representation," IEEE Transactions on Pattern analysis and Machine Intelligence, vol. 19, No. 7, pp. 696-710, Jul. 1997.
Moghaddam, Baback et al., "Beyond Eigenfaces: Probabilistic Matching for Face Recognition." MIT Media Laboratory Perceptual Computing Section Technical Report No. 443, 3rd IEEE International Conference on Automatic Face & Gesture Recognition, Nara, Japan, Apr. 1998, 6 pages.
Nair, Vinod and James J. Clark, "Automated Visual Surveillance Using Hidden Markov Models," Centre for Intelligent Machines, McGill University, 15th Vision Interface Conference, 2002, Calgary, Canada, 5 pages.
Niebles, Juan Carlos et al., "A Hierarchical Model of Shape and Appearance for Human Action Classification," IEEE Conference on Computer Vision and Pattern Recognition, CVPR '07, Jun. 17-22, 2007, pp. 1-8, IEEE.
PCT/US10/56383 International Search Report and Written Opinion of the International Searching Authority, mailed Feb. 21, 2011, 13 pages.
PCT/US10/56405 International Search Report and Written Opinion of the International Searching Authority, mailed Feb. 18, 2011, 12 pages.
Rabiner, Lawrence R., "A Tutorial on Hidden Markov Models and Selected Applications in Speech Recognition," Proceedings of IEEE, vol. 77, No. 2, Feb. 1989, pp. 257-286.
Sánchez-Nielsen, Elena et al., "Hand Gesture Recognition for Human-Machine Interaction," Journal of WSCG, Feb. 2-6, 2003, 8 pages, vol. 12, No. 1-3, Union Agency—Science Press, Plzen, Czech Republic.
Segen, Jakub and Senthil Kumar, "Shadow Gestures: 3D Hand Pose Estimation using a Single Camera," IEEE Computer Society Conference on Computer Vision and Pattern Recognition, Jun. 1999, 7 pages, IEEE.
Song, Cindy, et al., "Video Hand Gesture Interface," 2006, 22 pages, University of Berkeley, Berkeley, CA, USA.
Starner, Thad Eugene, Visual Recognition of American Sign Language Using Hidden Markov Models, Master's Thesis, School of Architecture and Planning, Massachusetts Institute of Technology, Feb. 1995, 52 pages.
Vertut, Jean and Phillipe Coiffet, *Robot Technology: Teleoperation and Robotics Evolution and Development*, English translation, Prentice-Hall, Inc., Inglewood Cliffs, NJ, USA 1986, vol. 3A, 332 pages.
Wachs, Juan P. et al., "A Gesture-Based Tool for Sterile Browsing of Radiology Images," Journal of the American Medical Informatics Association, vol. 15, No. 3, May/Jun. 2008, pp. 321-323.
Zyout, Imad et al., "Bayesian Classifier with Simplified Learning Phase for Detecting Microcalcifications in Digital Mammograms," International Journal of Biomedical Imaging, vol. 2009, Article ID 767805, 13 pages, Hindawi Publishing Corporation.
PCT/US09/56409 International Search Report and Written Opinion of the International Searching Authority, mailed Feb. 18, 2011, 13 pages.

\* cited by examiner

MASTER FINGER TRACKING DEVICE AND METHOD OF USE IN A MINIMALLY INVASIVE SURGICAL SYSTEM

CROSS-REFERENCE TO RELATED APPLICATION

This application is a continuation-in-part of U.S. patent application Ser. No. 12/617,937 (filed 13 Nov. 2009, disclosing "Patient-Side Surgeon Interface For a Minimally Invasive Teleoperated Surgical Instrument"), which is incorporated herein by reference in its entirety

BACKGROUND

1. Field of Invention

Aspects of this invention are related to control of minimally invasive surgical systems, and are more particularly related to using hand movement of a surgeon in controlling a minimally invasive surgical system.

2. Related Art

Method and techniques for tracking hand positions and gestures are known. For example, some video game controllers utilize hand tracking input. For example, the Nintendo Wii® gaming platform supports wireless position and orientation sensing remote controls. (Wii is a registered trademark of Nintendo of America Inc, Redmond Wash., U.S.A.) The use of gestures and other physical motions like swinging a bat or waving a magic wand provide the fundamental gaming element for this platform. The Sony Playstation Move has features similar to those of the Nintendo Wii® gaming platform.

A wireless CyberGlove® motion capture data glove from CyberGlove Systems includes eighteen data sensors with two bend sensors on each finger, four abduction sensors and sensors measuring thumb crossover, palm arch, wrist flexion, and wrist abduction. (CyberGlove® is a registered trademark of CyberGlove Systems LLC of San Jose, Calif.) When a three-dimensional tracking system is used with the CyberGlove® motion capture data glove, x, y, z, yaw, pitch, roll position, and orientation information for the hand are available. The motion capture system for the CyberGlove® motion capture data glove has been used in digital prototype evaluation, virtual reality biomechanics, and animation.

Another data glove with forty sensors is the ShapeHand data glove of Measurand Inc. A ShapeClaw portable, lightweight hand motion capture system of Measurand Inc. includes a system of flexible ribbons that capture index finger and thumb motion along with position and orientation of the hand and forearm in space.

In In-Cheol Kim and Sung-Il Chien, "*Analysis of 3D Hand Trajectory Gestures Using Stroke-Based Composite Hidden Markov Models*", Applied Intelligence, Vol. 15 No. 2, p. 131-143, September-October 2001, Kim and Chien explore the use of three-dimensional trajectory input with a Polhemus sensor for gesture recognition. Kim and Chien propose this form of input because three-dimensional trajectories offer more discriminating power than two-dimensional gestures, which are predominantly used in video-based approaches. For their experiments, Kim and Chien made use of a Polhemus magnetic position tracking sensor attached to the back of a Fakespace PinchGlove. The PinchGlove provides a means for the user to signal the beginning and ending of a gesture while the Polhemus sensor captures the three-dimensional trajectory of the user's hand.

In Elena Sanchez-Nielsen, et al., "*Hand Gesture Recognition for Human-Machine Interaction*," Journal of WSCG, Vol. 12, No. 1-3, ISSN 1213-6972, WSCG '2004, Feb. 2-6 20003, Plzen Czech Republic, a real time vision system is proposed for application within visual interaction environments through hand gesture recognition using general purpose hardware and low cost sensors, like a personal computer and a web cam. In Pragati Garg, et al., "*Vision Based Hand Gesture Recognition,*" 49 World Academy of Science, Engineering and Technology, 972-977 (2009), a review of vision-based hand gesture recognition was presented. One conclusion presented was that most approaches rely on several underlying assumptions that may be suitable in a controlled lab setting but do not generalize to arbitrary settings. The authors stated "Computer Vision methods for hand gesture interfaces must surpass current performance in terms of robustness and speed to achieve interactivity and usability." In the medical area, gesture recognition has been considered for sterile browsing of radiology images. See Juan P. Wachs, et al., "A Gesture-based Tool for Sterile Browsing of Radiology Images", Journal of the American Medical Informatics Association (2008; 15:321-323, DOI 10.1197/jamia.M24).

SUMMARY

In one aspect, a hand tracking system in a minimally invasive surgical system tracks a location of part of a human hand. A system control parameter of the minimally invasive surgical system is generated based on the location of the part of the human hand. Operation of the minimally invasive surgical system is controlled using the system control parameter.

In one aspect, sensor elements mounted on part of a human hand are tracked to obtain locations of the part of the human hand. A position and an orientation of a control point are generated based on the location. Teleoperation of a device in a minimally invasive surgical system is controlled based on the control point position and orientation. In one aspect, the device is a teleoperated slave surgical instrument. In another aspect, the device is a virtual proxy presented in a video image of a surgical site. Examples of a virtual proxy include a virtual slave surgical instrument, a virtual hand, and a virtual telestration device.

In a further aspect, a grip closure parameter is generated in addition to the position and orientation of the control point. The grip of an end effector of the teleoperated slave surgical instrument is controlled based on the grip closure parameter In another aspect, the system control parameter is a position and an orientation of a control point used for teleoperation of the slave surgical instrument. In yet another aspect, the system control parameter is determined from two hands. The system control parameter is a position and an orientation of a control point for one of the two hands, and a position and an orientation of a control point for the other of the two hands. The control points are used for teleoperation of an endoscopic camera manipulator in the minimally invasive surgical system.

In still another aspect, sensor elements mounted on part of a second human hand are tracked in addition to the sensor elements on the part of the human hand. A position and an orientation of a second control point are generated based on the location of the part of the second human hand. In this aspect, both the control point and the second control point are used in the teleoperation control.

In yet another aspect, sensor elements mounted on digits of a human hand are tracked. A motion between the digits is determined, and orientation of a teleoperated slave surgical instrument in a minimally invasive surgical system is controlled based on the motion.

When the motion is a first motion, the controlling includes rolling a tip of a slave surgical instrument wrist about its pointing direction. When the motion is a second motion different from the first motion, the controlling includes yaw motion of the slave surgical instrument wrist.

A minimally invasive surgical system includes a hand tracking system and a controller coupled to the hand tracking system. The hand tracking system tracks locations of a plurality of sensor elements mounted on part of a human hand. The controller transforms the locations to a position and an orientation of a control point. The controller sends a command to move a device in the minimally invasive surgical system based on the control point. Again, in one aspect, the device is a teleoperated slave surgical instrument, while in another aspect, the device is a virtual proxy presented in a video image of a surgical site.

In one aspect, the system also includes a master finger tracking device including the plurality of tracking sensors. The master finger tracking device further includes a compressible body, a first finger loop affixed to the compressible body, and a second finger loop affixed to the compressible body. A first tracking sensor in the plurality of tracking sensors is attached to the first finger loop. A second tracking sensor in the plurality of tracking sensors is attached to the second finger loop.

Hence, in one aspect, a minimally invasive surgical system includes a master finger tracking device. The master finger tracking device includes a compressible body, a first finger loop affixed to the compressible body, and a second finger loop affixed to the compressible body. A first tracking sensor is attached to the first finger loop. A second tracking sensor is attached to the second finger loop.

The compressible body includes a first end, a second end, and an outer exterior surface. The outer exterior surface includes a first portion extending between the first and second ends, and a second portion, opposite and removed from the first portion, extending between the first and second ends.

The compressible body also has a length. The length is selected to limit a separation between a first digit and as second digit of the human hand.

The first finger loop is affixed to the compressible body adjacent to the first end and extends about the first portion of the outer exterior surface. Upon placement of the first finger loop on a first digit of a human hand, a first part of the first portion of the outer exterior surface contacts the first digit.

The second finger loop is affixed to the compressible body adjacent to the second end and extends about the first portion of the outer exterior surface. Upon placement of the second finger loop on a second digit of the human hand, a second part of the first portion of the outer exterior surface contacts the second digit. Upon movement of the first and second digits towards each other, the compressible body is positioned between the two digits so that the compressible body provides resistance to the movement.

A thickness of the compressible body is selected so that upon a tip of the first digit just touching a tip of the second digit, the compressible body is less than fully compressed. The compressible body is configured to provide haptic feedback corresponding to a grip force of an end effector of a teleoperated slave surgical instrument.

In one aspect, the first and second tracking sensors are passive electromagnetic sensors. In a further aspect, each passive electromagnetic tracking sensor has six degrees of freedom.

A method of using the master finger tracking device includes tracking a first location of a sensor mounted on a first digit of a human hand and a second location of another sensor mounted on a second digit. Each location has N degrees of freedom, where N is an integer number greater than zero. The first location and the second location are mapped to a control point location. The control point location has six degrees of freedom. The six degrees of freedom are less than or equal to 2*N degrees of freedom. The first location and the second location are also mapped to a parameter having a single degree of freedom. Teleoperation of a slave surgical instrument in a minimally invasive surgical system is controlled based on the control point location and the parameter.

In a first aspect, the parameter is a grip closure distance. In a second aspect, the parameter comprises an orientation. In another aspect, N is six, while in a different aspect, N is five.

In yet a further aspect, sensor elements mounted on part of a human hand are tracked to obtain a plurality of locations of the part of the human hand. A hand gesture from a plurality of known hand gestures is selected based on the plurality of locations. Operation of a minimally invasive surgical system is controlled based on the hand gesture.

The hand gesture can be any one of a hand gesture pose, a hand gesture trajectory, or a combination of a hand gesture pose and a hand gesture trajectory. When the hand gesture is a hand gesture pose and the plurality of known hand gestures includes a plurality of known hand gesture poses, a user interface of the minimally invasive surgical system is controlled based on the hand gesture pose.

Further, in one aspect, when the hand gesture is hand gesture pose, the hand gesture selection includes generating an observed feature set from the tracked plurality of locations. The observed feature set is compared with feature sets of the plurality of known hand gesture poses. One of the known hand gesture is selected as the hand gesture pose. The selected known hand gesture pose is mapped to a system command, and the system command is triggered in the minimally invasive surgical system.

In yet a further aspect, when the hand gesture includes a hand gesture trajectory, the user interface of the minimally invasive surgical system is controlled based on the hand gesture trajectory.

In the minimally invasive surgical system with the hand tracking systems and the controller, the controller transforms the locations to a hand gesture. The controller sends a command to modify a mode of operation of the minimally invasive surgical system based on the hand gesture.

In still another aspect, a sensor element mounted on part of a human is tracked to obtain a location of the part of the human hand. Based on the location, the method determines whether a position of the part of the human hand is within a threshold distance from a position of a master tool grip of a minimally invasive surgical system. Operation of the minimally invasive surgical system is controlled based on a result of the determining. In one aspect, teleoperation of a teleoperated slave surgical instrument coupled to the master tool grip is controlled based on a result of the determination. In another aspect, display of a user interface, or display of a proxy visual is controlled based on the result of the determination.

In one aspect, the position of the part of the human hand is specified by a control point position. In another aspect, the position of the part of the human hand is an index finger position.

A minimally invasive surgical system includes a hand tracking system. The hand tracking system tracks a location of part of a human hand. A controller uses the location in determining whether a hand of a surgeon is close enough to a master tool grip to permit a particular operation of the minimally invasive surgical system.

A minimally invasive surgical system also includes a controller coupled to the hand tracking system. The controller converts the location to a system control parameter, and injects into the minimally invasive surgical system a command based on the system control parameter.

Figure 1:
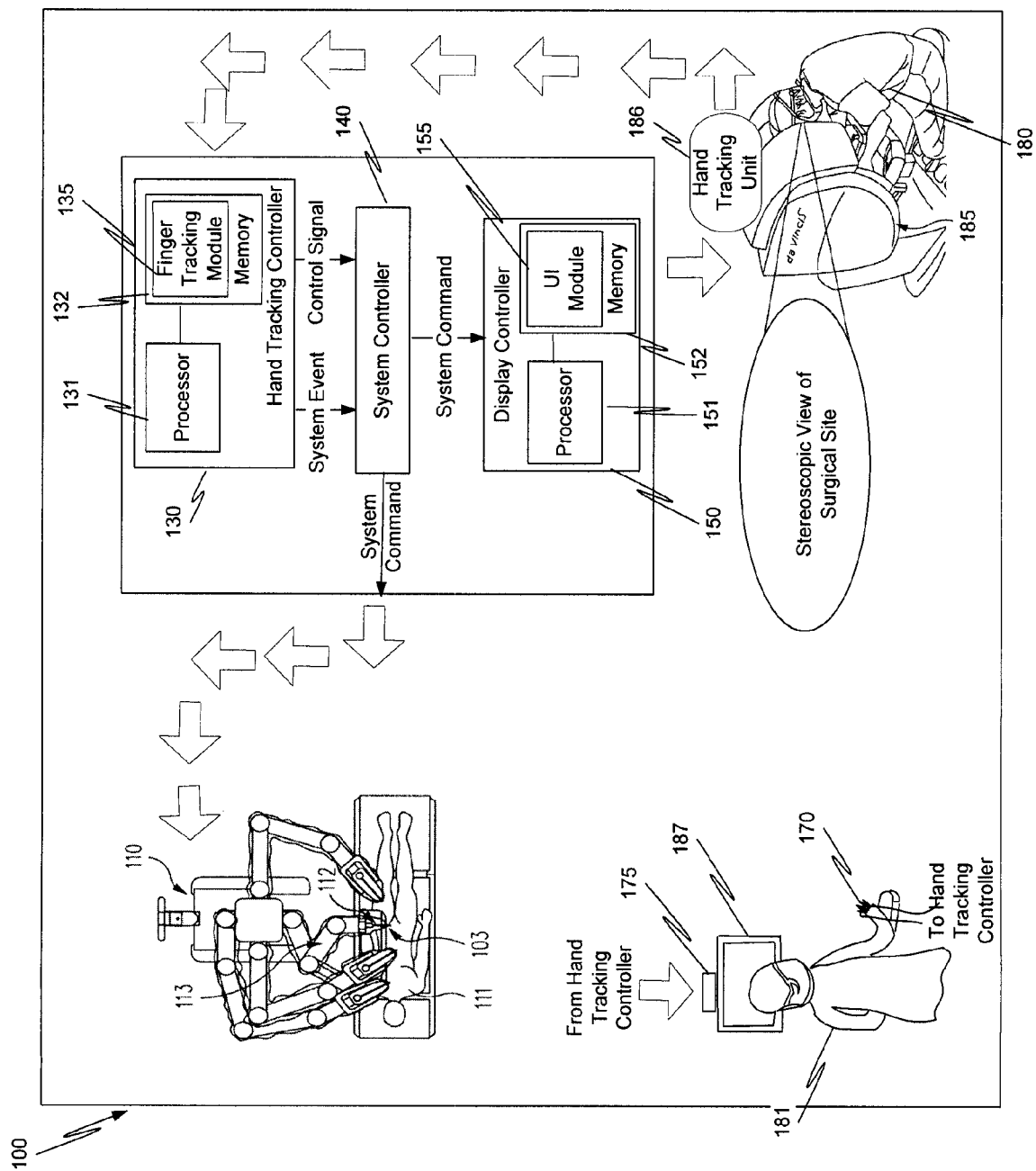
FIG. 1 is a high level diagrammatic view of a minimally invasive teleoperated surgical system including a hand tracking system.

In the drawings, the first digit of a three digit reference number indicates the figure number of the figure in which the element with that reference number first appeared and the first two digits of a four digit reference number indicate the figure number of the figure in which the element with that reference number first appeared.

DETAILED DESCRIPTION

As used herein, a location includes a position and an orientation.

As used herein, a hand gesture, sometimes called a gesture, includes a hand gesture pose, a hand gesture trajectory, and a combination of a hand gesture pose and a hand gesture trajectory.

Aspects of this invention augment the control capability of minimally invasive surgical systems, e.g., the da Vinci® minimally invasive teleoperated surgical system commercialized by Intuitive Surgical, Inc. of Sunnyvale, Calif., by utilizing hand location information in controlling the minimally invasive surgical system. A measured location of one or more digits of the hand is used to determine a system control parameter that in turn is used to trigger a system command in the surgical system. The system commands depend on the location of the person whose hand location is being tracked, i.e., whether the person is at a surgeon's console.

When the measured locations are for digits of a hand of a person not at a surgeon's console, the system commands include a command to change orientation of a part of a teleoperated slave surgical instrument based on a combination of hand orientation and relative motion of a two digits of a hand, and a command to move a tip of a teleoperated slave surgical instrument so that the motion of the tip follows motion of a part of the hand. When the measured locations are for digits of a hand of a person at a surgeon's console, the system commands include commands permitting or preventing motion of a slave surgical instrument to continue to follow motion of a master tool grip. When the measured locations are either for digits of a hand of a person not at a surgeon's console, or for digits of a hand of a person at a surgeon's console, the system commands include commanding the system, or a part of the system to take an action based on a hand gesture pose, and commanding the system or a part of the system to take an action based on a hand gesture trajectory.

FIG. 1 is a high level diagrammatic view of a minimally invasive teleoperated surgical system 100, for example, the da Vinci® Surgical System, including a hand tracking system. There are other parts, cables etc. associated with the da Vinci® Surgical System, but these are not illustrated in FIG. 1 to avoid detracting from the disclosure. Further information regarding minimally invasive surgical systems may be found for example in U.S. patent application Ser. No. 11/762,165 (filed Jun. 13, 2007, disclosing "Minimally Invasive Surgical System"), and U.S. Pat. No. 6,331,181 (issued on Dec. 18, 2001, disclosing "Surgical Robotic Tools, Data Architecture, And Use"), both of which are incorporated herein by reference. See also e.g., U.S. Pat. No. 7,155,315 (filed Dec. 12, 2005; disclosing "Camera Referenced Control In A Minimally Invasive Surgical Apparatus") and U.S. Pat. No. 7,574,250 (filed Feb. 4, 2003; disclosing "Image Shifting Apparatus And Method For A Telerobotic System"), which are both incorporated herein by reference.

In this example, system 100 includes a cart 110 with a plurality of manipulators. Each manipulator and the teleoperated slave surgical instrument controlled by that manipulator can be coupled to and decoupled from master tool manipulators on surgeon's console 185, and in addition they can be coupled to and decoupled from mechanically ungrounded unpowered master finger tracking grip 170, sometimes called master finger tracking grip 170.

A stereoscopic endoscope 112 mounted on manipulator 113 provides an image of surgical site 103 within patient 111 that is displayed on display 187 and on the display in surgeon's console 185. The image includes images of any of the slave surgical devices in the field of view of stereoscopic endoscope 112. The interactions between the master tool manipulators on surgeon's console 185, the slave surgical devices and stereoscopic endoscope 112 are the same as in a known system and so are known to those knowledgeable in the field.

In one aspect, surgeon 181 moves at least one digit of the surgeon's hand, which in turn causes a sensor in master finger tracking grip 170 to change location. Hand tracking transmitter 175 provides a field so that the new position and orientation of the digit is sensed by master finger tracking grip 170. The new sensed position and orientation are provided to hand tracking controller 130.

In one aspect, as explained more completely below, hand tracking controller 130 maps the sensed position and orientation to a control point position and a control point orientation in an eye coordinate system of surgeon 181. Hand tracking controller 130 sends this location information to system controller 140 that in turn sends a system command to the teleoperated slave surgical instrument coupled to master finger tracking grip 170. As explained more completely below, using master finger tracking grip 170, surgeon 181 can control, for example, the grip of an end effector of the teleoperated slave surgical instrument, as well as the roll and yaw of a wrist coupled to the end effector.

In another aspect, hand tracking of at least a part of the hand of surgeon 181 or of the hand of surgeon 180 is used by hand tracking controller 130 to determine whether a hand gesture pose is made by the surgeon, or a combination of a hand gesture pose and a hand gesture trajectory is made by the surgeon. Each hand gesture pose and each trajectory combined with a hand gesture pose is mapped to a different system command. The system commands control, for example, system mode changes and control other aspects of minimally invasive surgical system 100.

For example in place of using foot pedals and switches as in a known minimally invasive surgical system, a hand gesture, either a hand gesture pose or a hand gesture trajectory, is used (i) to initiate following between motions of the master tool grip and the associated teleoperated slave surgical instrument, (ii) for master clutch activation (which decouples master control of the slave instrument), (iii) for endoscopic camera control (which allows the master to control endoscope movement or features, such as focus or electronic zoom), (iv) for robotic arm swap (which swaps a particular master control between two slave instruments), and (v) for TILEPRO™ swap, (which toggles the display of auxiliary video windows on the surgeon's display). (TILEPRO is a trademark of Intuitive Surgical, Inc. of Sunnyvale, Calif., USA.)

When there are only two master tool grips in system 100 and surgeon 180 wants to control movement of a slave surgical instrument other than the two teleoperated slave surgical instruments coupled to the two master tool grips, the surgeon may lock one or both of the two teleoperated slave surgical instruments in place using a first hand gesture. The surgeon then associates one or both of the master tool grips with other slave surgical instruments held by other of the manipulator arms by using a different hand gesture that in this implementation provides swap association of the master tool grip to another teleoperated slave surgical instrument. Surgeon 181 performs an equivalent procedure when there are only two master finger tracking grips in system 100.

In yet another aspect, a hand tracking unit 186 mounted in surgeon's console 185 tracks at least a part of the hand of surgeon 180 and sends the sensed location information to hand tracking controller 130. Hand tracking controller 130 determines when the surgeon's hand is close enough to the master tool grip to permit system following, e.g., the motion of the slave surgical instrument follows the motion of the master tool grip. As explained more completely below, in one aspect, hand tracking controller 130 determines the position of the surgeon's hand and the position of the corresponding master tool grip. If the difference in the two positions is within a predetermined distance, e.g., less than a threshold separation, following is permitted, and otherwise following is inhibited. Thus, distance is used as a measure of presence of the surgeon's hand with respect to the master tool grip on surgeon's console 185. In another aspect, when the position of the surgeon's hand relative to the position of the master tool grip is less than the threshold separation, display of a user interface on a display is inhibited, e.g., turned off on a display device. Conversely, when the position of the surgeon's hand relative to the position of the master tool grip is greater than the threshold separation, the user interface is displayed on the display device, e.g., turned on.

Presence detection of the surgeon's hand has been a long standing problem. Presence detection has been attempted many times using different contact sensing technologies, such as capacitive switches, pressure sensors, and mechanical switches. However, these approaches are inherently problematic because surgeons have different preferences in how and where they hold the master tool grip. Using distance as a measure of presence is advantageous because this type of presence detection allows the surgeon to touch the master tool grip lightly and then momentarily break physical contact to adjust the master tool grip, but it does not constrain how the surgeon holds the master tool grip with his/her fingers.

Surgical Instrument Control via Hand Tracking

One example of a mechanically ungrounded unpowered master finger tracking grip 270, sometimes called master finger tracking grip 270, is illustrated in FIGS. 2A to 2D in different configurations that are described more completely below. Master finger tracking grip 270 includes digit mounted sensors 211, 212, sometimes referred to as finger and thumb mounted sensors 211, 212, which independently track the location (position and orientation in one example) of each of a tip of index finger 292B and a tip of thumb 292A, i.e., track the location of two digits of the surgeon's hand. Thus, the location of the hand itself is tracked as opposed to tracking the location of master tool grips in a known minimally invasive surgical system.

In one aspect, the sensors provide tracking of six degrees of freedom (three translation and three rotation) for each digit of the hand upon which a sensor is mounted. In another aspect, the sensors provide tracking of five degrees of freedom (three translation and two rotation) for each digit of the hand upon which a sensor is mounted.

In still yet another aspect, the sensors provide tracking of three degrees of freedom (three translation) for each digit of the hand upon which a sensor is mounted. When two digits are each tracked with three degrees of freedom, the total six translational degrees of freedom are sufficient to control a slave surgical instrument that does not include a wrist mechanism.

A padded foam connector 210 is connected between finger and thumb mounted sensors 211, 212. Connector 210 constrains thumb 292A and index finger 292B, i.e., the digits of hand 291R, to be within a fixed distance, i.e., there is a maximum separation distance between the digits of hand 291R upon which master finger tracking grip 270 is mounted. As thumb 292A and forefinger 292B are moved from the maximum separation (FIG. 2A) to a completely closed configuration (FIG. 2D), the padding provides positive feedback to help surgeon 181 control the grip force of an end effector of a teleoperated slave surgical instrument coupled to master finger tracking grip 170.

Figure 2A:
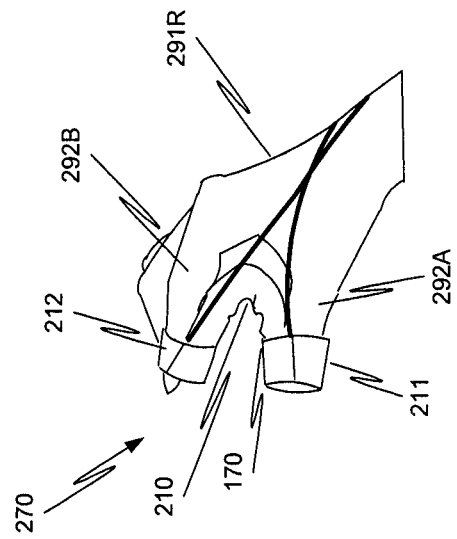
FIGS. 2A to 2G are examples of various configurations of a hand-tracked master tool grip used to control a teleoperated slave surgical instrument of the minimally invasive teleoperated surgical system of FIG. 1.
Figure 2B:
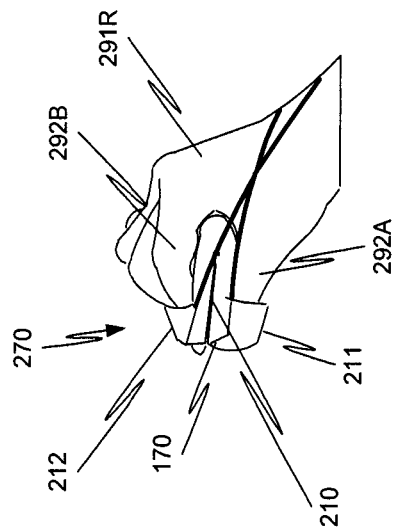
Figure 2C:
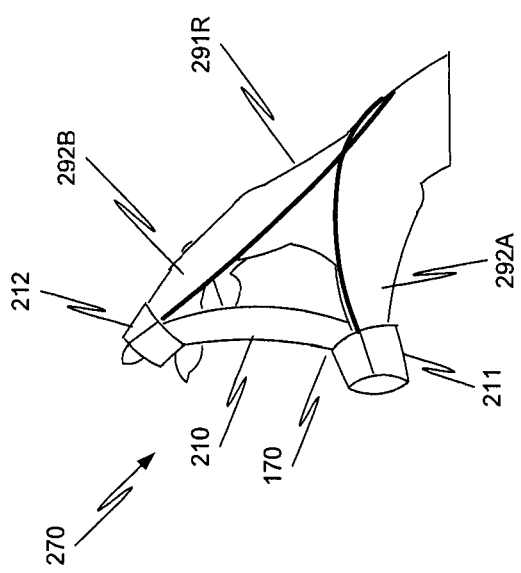

For the position illustrated in FIG. 2A with thumb 292A and forefinger 292B separated by the maximum distance permitted by master finger tracking grip 270, the grip force is a minimum. Conversely, in the position illustrated in FIG. 2D where thumb 292A and forefinger 292 are as close as permitted by connector 210, i.e., separated by a minimum distance permitted by master finger tracking grip 270, the grip force is a maximum. FIGS. 2B and 2C represent positions that are mapped to intermediate grip forces.

As explained more completely below, the locations (positions and orientations) of thumb 292A and forefinger 292B in FIGS. 2A to 2D are mapped to a grip closure parameter, e.g., a normalized grip closure value that is used to control the grip of the teleoperated slave surgical instrument coupled to master finger tracking grip 270. Specifically, the sensed locations of thumb 292A and forefinger 292B are mapped to the grip closure parameter by hand tracking controller 130.

Thus, a location of a part of the hand of surgeon 181 is tracked. Based on the tracked location, a system control parameter of minimally invasive surgical system 100, i.e., a grip closure parameter, is generated by hand tracking controller 130, and supplied to system controller 140. System controller 140 uses the grip closure parameter in generating a system command that is sent to the teleoperated slave surgical instrument. The system command instructs the teleoperated surgical instrument to configure an end effector to have a grip closure corresponding to the grip closure parameter. Hence, minimally invasive surgical system 100 uses the grip closure parameter to control operation of the teleoperated slave surgical instrument of minimally invasive surgical system 100.

Also, the locations (position and orientation) of thumb 292A and forefinger 292B in FIGS. 2A to 2D are mapped to a control point position and a control point orientation by hand tracking controller 130. The control point position and control point orientation are mapped into an eye coordinate system for surgeon 181, and then provided to system controller 140 via a command signal. The control point position and control point orientation in the eye coordinate system are used by system controller 140 for teleoperation of the slave surgical instrument coupled to master finger tracking grip 170.

Again, a location of a part of the hand of surgeon 181 is tracked. Based on the tracked location, another system control parameter of minimally invasive surgical system 100, i.e., the control point position and orientation, is generated by hand tracking controller 130. Hand tracking controller 130 transmits a command signal with the control point position and orientation to system controller 140. System controller 140 uses the control point position and orientation in generating a system command that is sent to the teleoperated slave surgical instrument. The system command instructs the teleoperated surgical instrument to position the teleoperated surgical instrument based on the control point position and orientation. Hence, minimally invasive surgical system 100 uses the control point position and orientation to control operation of the teleoperated slave surgical instrument of minimally invasive surgical system 100.

In addition to determining grip closure based on the positions of sensors 211, 212, other relative motion between forefinger 292B and thumb 292A is used to control the yaw motion and the roll motion of the slave surgical instrument. Rubbing together crosswise of finger 292B and thumb 292A as if spinning a spindle, which is represented by the arrows in (FIG. 2E) about an imaginary spindle 293, produces roll of the slave surgical instrument tip, while sliding the index finger and thumb up and back lengthwise along each other, which is represented by the arrows in (FIG. 2F) along an axis in the pointing direction represented by arrow 295, produces yaw motion along the X-axis of the slave surgical instrument. This is achieved by mapping the vector between the index finger tip and thumb tip positions to define the X-axis of the control point orientation. The position of the control point remains relatively stationary since the finger and thumb are each sliding in a symmetric manner along axis 295. While the motions of the finger and thumb are not completely symmetrical motions, the position still remains sufficiently stationary that the user can easily correct any perturbation that may occur.

Again, locations of a part of the hand of surgeon 181 are tracked. Based on the tracked locations, yet another system control parameter, i.e., the relative motion between two digits of surgeon's hand 291R, is generated by hand tracking controller 130.

Hand tracking controller 130 converts the relative motion into an orientation for the teleoperated slave surgical instrument coupled to master finger tracking grip 170. Hand tracking controller 130 sends a command signal with the orientation to system controller 140. While this orientation is an absolute orientation mapping, system controller 140, in one aspect, uses this input with ratcheting during teleoperation in the same matter as an orientation input from any other passive gimbal master tool grip. One example of ratcheting is described in commonly assigned U.S. patent application Ser. No. 12/495,213 (filed on Jun. 30, 2009, disclosing "Ratcheting For Master Alignment Of A Teleoperated Surgical Instrument"), which is incorporated herein by reference in its entirety.

System controller 140 uses the orientation in generating a system command that is sent to the teleoperated slave surgical instrument. The system command instructs the teleoperated surgical instrument to rotate the teleoperated surgical instrument based on the orientation. Hence, minimally invasive surgical system 100 uses the motion between the two digits to control of operation of the teleoperated slave surgical instrument of minimally invasive surgical system 100.

When the motion is a first motion, e.g., crosswise rubbing of finger 292B and thumb 292A as if spinning a spindle, the orientation is a roll, and the system command results in a tip roll of the slave surgical instrument wrist along its pointing direction. When the motion is a second motion different from the first motion, e.g., sliding the index finger and thumb up and back lengthwise along each other (FIG. 2F), the orientation is a yaw, and the system command results in a yaw motion of the slave surgical instrument wrist.

Figure 2D:
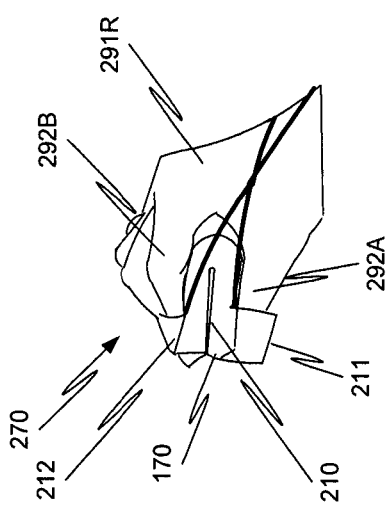
Figure 2E:
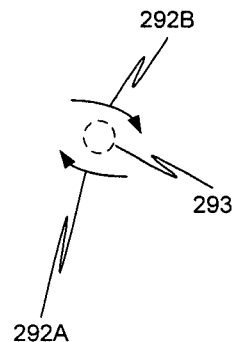
Figure 2F:
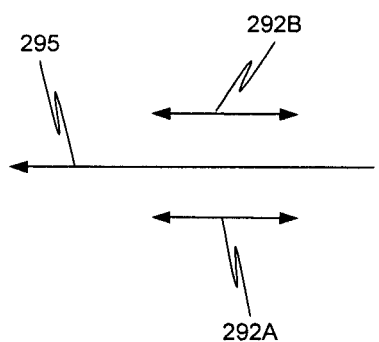
Figure 2G:
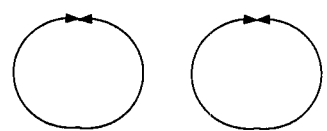
Figure 3A:
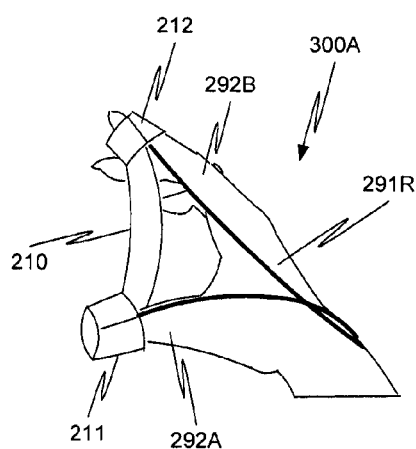
FIGS. 3A to 3D are examples of hand gesture poses used to control system modes in the minimally invasive teleoperated surgical system of FIG. 1.
Figure 3B:
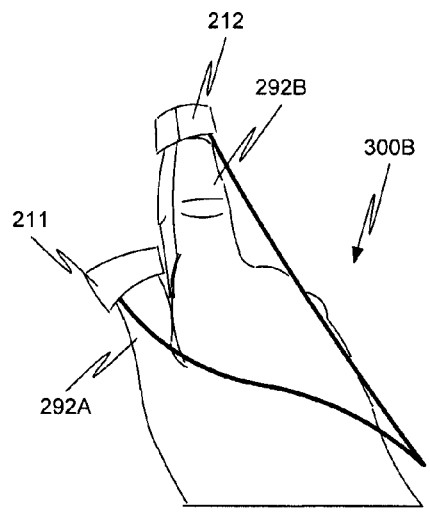
Figure 3C:
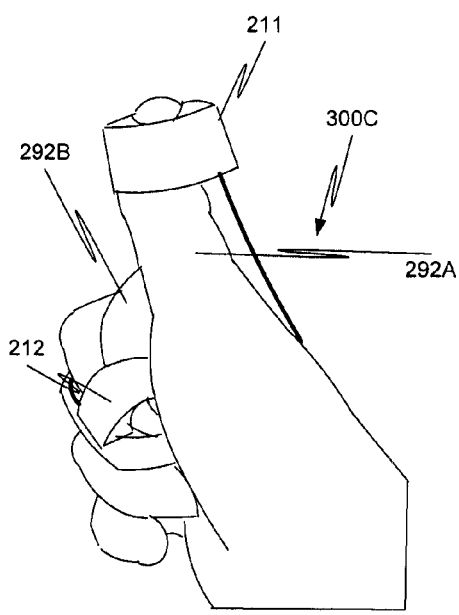
Figure 3D:
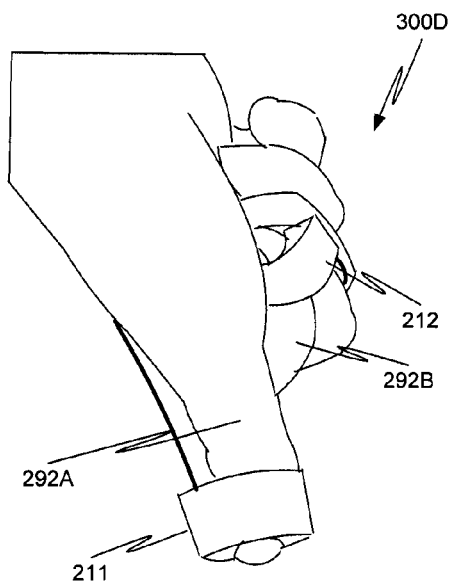

In yet another aspect, when the surgeon changes the system operation mode to a gesture recognition mode, both hands are tracked and control points and orientations for both hands are generated based on the sensed positions and orientations of the sensors mounted on the hands in one aspect. For example, as illustrated in FIG. 2G, the tips of the thumb and the forefinger of each hand are touched together to form a circular-like shape. The sensed position of each hand is mapped by hand tracking controller 130 to a pair of control point positions. The pair of control points is sent with a camera control system event to system controller 140.

Thus, in this aspect, a location of a part of each hand of surgeon 181 is tracked. Another system control parameter of minimally invasive surgical system 100, i.e., the pair of control point positions, based on the tracked location is generated by hand tracking controller 130. Hand tracking controller 130 sends the pair of control point positions with a camera control system event to system controller 140.

In response to the camera control system event, system controller 140 generates a camera control system command based on the pair of control point positions. The camera control system command is sent to a teleoperated endoscopic camera manipulator in minimally invasive surgical system 100. Hence, minimally invasive surgical system 100 uses the pair of control point positions to control operation of the teleoperated endoscopic camera manipulator of minimally invasive surgical system 100.

System Control via Hand Gesture Poses and Hand Gesture Trajectories

In this aspect, after being placed in a gesture detection mode of operation, hand tracking controller 130 detects a hand gesture pose, or a hand gesture pose and a hand gesture trajectory. Controller 130 maps hand gesture poses to certain system mode control commands, and similarly controller 130 maps hand gesture trajectories to other system mode control commands. Note that the mapping of poses and trajectories is independent and so this is different from, for example, manual signal language tracking. The ability to generate system commands and to control system 100 using hand gesture poses and hand gesture trajectories, in place of manipulating switches, numerous foot pedals, etc. as in known minimally invasive surgical systems, provides greater ease of use of system 100 for the surgeon.

When a surgeon is standing, the use of hand gesture poses and hand gesture trajectories to control system 100 makes it is unnecessary for the surgeon to take the surgeon's eyes off the patient and/or viewing screen and to search for a foot petal or a switch when the surgeon wants to change the system mode. Finally, the elimination of the various switches and foot pedals reduces the floor space required by the minimally invasive teleoperated surgical system.

The particular set of hand gesture poses and hand gesture trajectories used to control minimally invasive surgical system 100 are not critical so long as each hand gesture pose and each hand gesture trajectory is unambiguous. Specifically, one hand gesture pose should not be able to be interpreted by hand tracking controller 130 as one or more other hand gesture poses in the set of poses, and one hand gesture trajectory should not be interpreted as more than one hand gesture trajectory in the set of trajectories. Thus, the hand gesture poses and hand gesture trajectories discussed below are illustrative only and are not intended to be limiting.

Figure 4A:
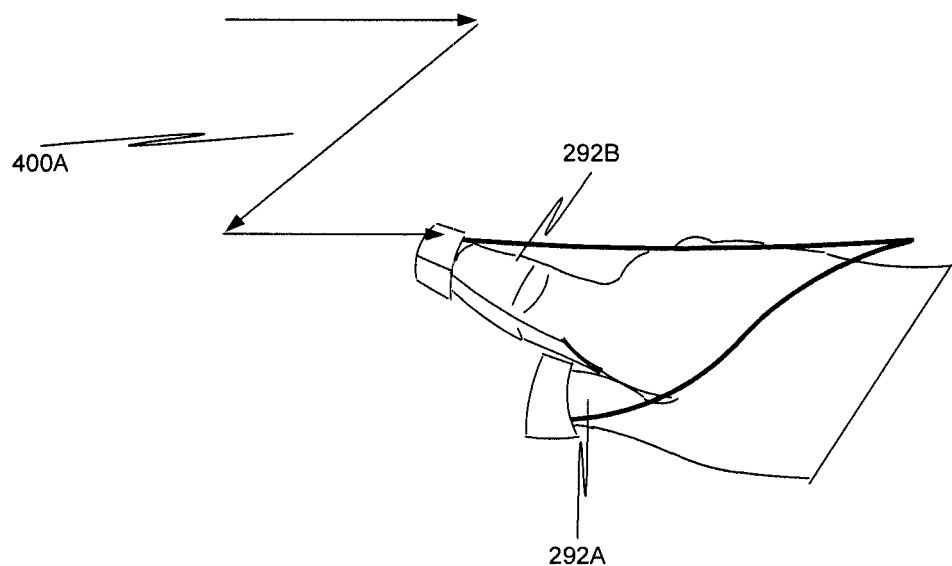
FIGS. 4A to 4C are examples of hand gesture trajectories that also are used to control system modes in the minimally invasive teleoperated surgical system of FIG. 1.
Figure 4B:
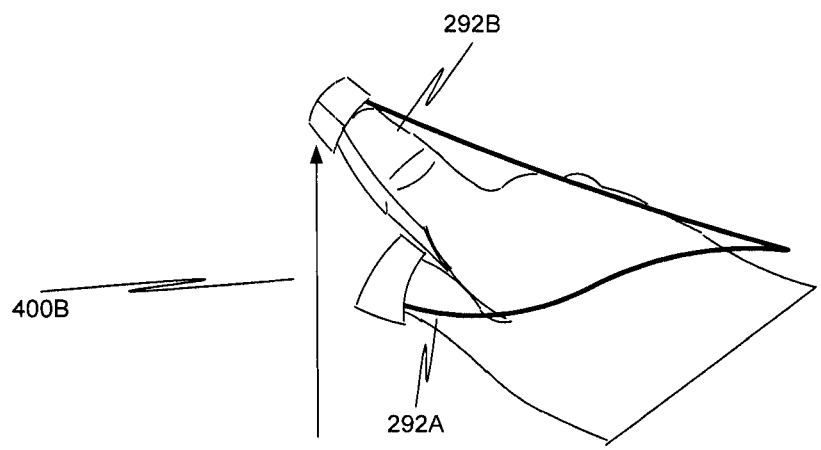
Figure 4C:

FIGS. 3A to 3D are examples of hand gesture poses 300A to 300D, respectively. FIGS. 4A to 4C are examples of hand gesture trajectories. Note, for example, that the configuration in FIG. 2A appears similar to that in FIG. 3A, but the operating mode of minimally invasive surgical system 100 is different when the two configurations are used.

In FIG. 2A, the teleoperated minimally invasive slave surgical instrument is coupled to master finger tracking grip 170 and system 100 is in the following mode so that movement of the teleoperated minimally invasive slave surgical instrument follows the tracked movement of the surgeon's hand. In FIGS. 3A to 3D and 4A to 4C, the surgeon places system 100 in gesture recognition mode, and then makes one of the illustrated hand gesture poses or hand gesture trajectories. The hand gesture poses and hand gesture trajectories are used in control of the system modes and are not used in the following mode of operation. For example, the system modes controlled with hand gesture poses are to enable, disable, and cycle between visuals displays, to clutch the visual display, and to draw/erase telestration.

In hand gesture pose 300A (FIG. 3A), thumb 292A and index finger 292 are separated beyond a master clutch threshold, e.g., the spread between the two digits of hand 291R is greater than 115 mm. Hand gesture pose 300B (FIG. 3B) with index finger 292B extended and thumb 292A curled is used to signal hand tracking controller 130 that the surgeon is tracing a hand gesture trajectory (See FIGS. 4A and 4B). Hand gesture pose 300C (FIG. 3C) with thumb 292A up and index finger 292B curled is used to turn on a user interface and to cycle between modes in the user interface. Hand gesture pose 300D (FIG. 3D) with thumb 292A down and index finger 292B curled is used to turn-off the user interface. Other hand gesture poses could include an "A-okay" hand gesture pose, an L-shaped hand gesture pose, etc.

Hand tracking controller 130, in one aspect, uses a multidimensional feature vector to recognize and identify a hand gesture pose. Initially, a plurality of hand gesture poses is specified. Next, a feature set that includes a plurality of features is specified. The feature set is designed to uniquely identify each hand gesture pose in the plurality of poses.

A hand gesture pose recognition process is trained using a training database. The training database includes a plurality of instances of each of the hand gesture poses. The plurality of instances includes feature vectors for the poses made by a number of different persons. A feature set is generated for each of the instances in the training database. These feature sets are used for training a multidimensional Bayesian classifier, as explained more completely below.

When surgeon 180 wants to enter the hand gesture mode of operation, the surgeon activates a switch, e.g., depresses a foot pedal, and then makes a hand gesture pose with at least one hand. Note that while this example requires a single foot petal, it allows the elimination of the other foot petals in the foot tray of the known minimally invasive surgical system and so still has the advantages described above. Hand tracking unit 186 sends signals representing the sensed positions and orientations of the thumb and index finger of the surgeon's hand or hands to hand tracking controller 130.

Using the tracking data for the digits of the surgeon's hand, hand tracking controller 130 generates an observed feature set. Hand tracking controller 130 then uses the trained multidimensional Bayesian classifier and a Mahalanobis distance to determine the likelihood, i.e., probability, that the observed feature set is a feature set of a hand gesture pose in the plurality of poses. This is done for each of the hand gesture poses in the plurality of poses.

The hand gesture pose in the plurality of poses that is selected by hand tracking controller 130 as the observed hand gesture pose is the one having the smallest Mahalanobis distance if the Mahalanobis distance is less than the maximum Mahalanobis distance in the training database for that hand gesture pose. The selected hand gesture pose is mapped to a system event. Hand tracking controller 130 injects the system event to system controller 140.

System controller 140 processes the system event and issues a system command. For example, if hand gesture pose 300C (FIG. 3C) is detected, system controller 140 sends a system command to display controller 150 to turn on the user interface. In response, display controller 150 executes at least a part of user interface module 155 on processor 151 to generate a user interface on the display of surgeon's console 185.

Thus, in this aspect, minimally invasive surgical system 100 tracks a location of part of a human hand. Based on the tracked location, a system control parameter is generated, e.g., a hand gesture pose is selected. The hand gesture pose is used to control the user interface of minimally invasive surgical system 100, e.g., display the user interface on the display of surgeon's console 185.

User interface control is illustrative only and is not intended to be limiting. A hand gesture can be used to perform any of the mode changes in a known minimally invasive surgical system, e.g., master clutch, camera control, camera focus, manipulator arm swapping, etc.

If the hand gesture pose recognition process determines that the observed hand gesture pose is the hand gesture pose for a hand gesture trajectory, a system event is not injected by hand tracking controller 130 based on the recognition of the pose. Instead, a hand gesture trajectory recognition process is initiated.

In this example, hand gesture pose 300B (FIG. 3B) is the pose used to generate a hand gesture trajectory. FIGS. 4A and 4B are two-dimensional examples of hand gesture trajectories 400A and 400B that are made using hand gesture pose 300B. FIG. 4C presents other two-dimensional examples of hand gesture trajectories that may be used.

In one aspect, the hand gesture trajectory recognition process uses a Hidden Markov Model Λ. To generate the probability distributions for Hidden Markov Model Λ, a training database is needed. Prior to obtaining the training database, a set of hand gesture trajectories are specified. In one aspect, the sixteen hand gesture trajectories of FIG. 4C are selected.

In one aspect, a number of test subjects are selected to make each of the hand gesture trajectories. In one example, each test subject performed each trajectory a predetermined number of times. The position and orientation data for each of the subjects for each trajectory performed was saved in the training database. In one aspect, as explained more completely below, the training database was used to train a discrete left-right Hidden Markov Model using an iterative Baum-Welch method.

When a surgeon makes a trajectory, the data is converted into an observation sequence o by hand tracking controller 130. With observation sequence o and Hidden Markov Model Λ, hand tracking controller 130 determines which hand gesture trajectory corresponds to the observed symbol sequence. In one aspect, hand tracking controller 130 uses the forward recursion algorithm with the Hidden Markov Model Λ to generate the total probability of the observed symbol sequence. The hand gesture trajectory with the highest probability is selected if that probability is greater than a threshold probability. If the highest probability is less than the threshold probability, no hand gesture trajectory is selected, and the processing ends.

The selected hand gesture trajectory is mapped to a system event. Hand tracking controller 130 injects the system event to system controller 140.

System controller 140 processes the system event and issues a system command. For example, if the selected hand gesture trajectory mapped to an event to change the illumination level on the surgical site, system controller 140 sends a system event to a controller in an illuminator to change the illumination level.

Presence Detection via Hand Tracking

Figure 6A:
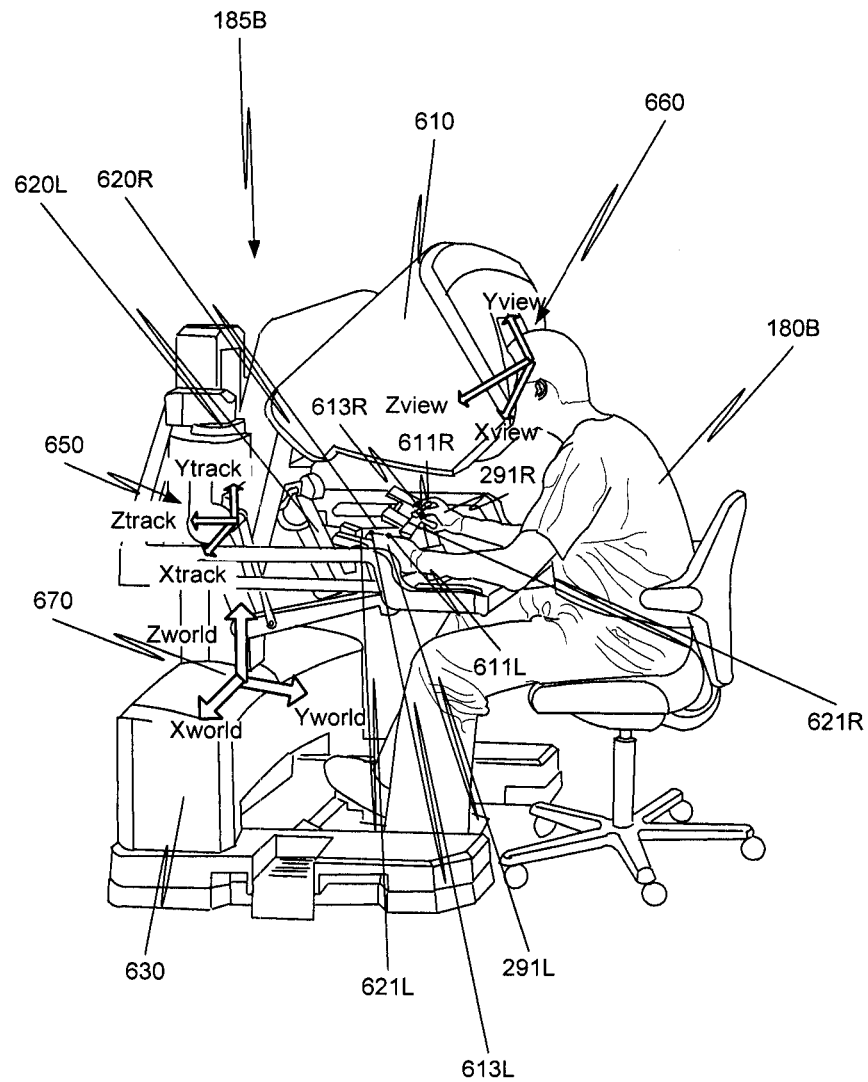
FIGS. 6A and 6B are more detailed diagrams of the surgeon's console of FIG. 1, and include examples of coordinate systems utilized in hand tracking by the minimally invasive teleoperated surgical system of FIG. 1.

In one aspect, as indicated above, the positions of surgeon's hands 291R, 291L (FIG. 6A) are tracked to determine whether teleoperation of minimally invasive surgical system 100 is permitted and in some aspects whether to display a user interface to the surgeon. Again, hand tracking controller 130 tracks at least a part of a hand of surgeon 180B (FIG. 6A). Hand tracking controller 130 generates a location of a master tool grip, e.g., master tool grip 621 (FIG. 6B), which represents master tool grips 621L, 621R (FIG. 6A), and a location of the part of the hand. Hand tracking controller 130 maps the two locations into a common coordinate frame and then determines the distance between the two locations in the common coordinate frame. The distance is a system control parameter of a minimally invasive surgical system that is based on the tracked location of the part of the surgeon's hand.

If the distance is less than a safe threshold, i.e., less than a maximum permitted separation between the part of the hand and the master tool grip, teleoperation of minimally invasive surgical system 100 is permitted, and otherwise, teleoperation is inhibited. Similarly, in the aspect that uses presence detection to control display of a user interface, if the distance is less than a safe threshold, i.e., less than a maximum permitted separation between the part of the hand and the master tool grip, display of a user interface on a display of minimally invasive surgical system 100 is inhibited, and otherwise the display of the user interface is permitted Thus, the distance is used in controlling teleoperation of minimally invasive surgical system 100. Specifically, hand tracking controller 130 sends a system event to system controller 140 indicating whether teleoperation is permitted. In response to the system event, system controller 140 configures system 100 to either allow or inhibit teleoperation.

Hand Location Tracking Technologies

Prior to considering the various aspects of hand tracking described above in further detail, one example of a tracking technology is described. This example is illustrative only and in view of the following description, any tracking technology that provides the necessary hand or finger location information can be utilized.

In one aspect, pulsed DC electromagnetic tracking is used with sensors mounted on two digits of a hand, e.g., the thumb and forefinger, as illustrated in FIGS. 2A to 2D and FIG. 7. Each sensor measures six degrees of freedom and in one aspect has a size of eight millimeters by two millimeters by one and one half millimeters (8 mm×2 mm×1.5 mm). The tracking system has a 0.8 m hemisphere dexterous workspace and a position sensing resolution of 0.5 mm and 0.1 degrees. The update rate is 160 Hertz and has a sensing latency of four milliseconds. When integrated into a system, additional latency may be incurred due to communication and additional filtering. Effective command latency up to 30 milliseconds has been found to be acceptable In this aspect, a tracking system includes an electromagnetic hand tracking controller, sensors for use in the master finger tracking grip, and a hand-tracking transmitter. A tracking system suitable for use in one embodiment of this invention is available from Ascension Technology Corporation of Burlington, Vt., USA as a 3D guidance trakSTAR™ System with a Mid-Range Transmitter. (trakSTAR™ is a trademark of Ascension Technology Corporation.) The transmitter generates pulsed DC magnetic fields for high accuracy tracking over medium ranges, which is specified as 78 centimeters (31 inches.) This system provides dynamic tracking with 240 to 420 updates/second for each sensor. The outputs of the miniaturized passive sensors are unaffected by power line noise sources. A clear line-of-sight between the transmitter and the sensors is not required. There is all attitude tracking and no inertial drift or optical interference. There is high metal immunity and no distortion from nonmagnetic metals.

While an electromagnetic tracking system with finger covers is used herein, this is illustrative only and is not intended to be limiting. For example, a pen-like device could be held by the surgeon. The pen-like device is a finger piece with three or more non-colinear fiducial markers on the external surface of the device. Typically, to make at least three fiducial markers visible at any viewpoint, more fiducial markers are used due to self occlusion. The fiducial markers are sufficient to determine six degrees of freedom (three translation and three rotation) motion of the finger piece and thus that of the hand holding the pen-like device. The pen-like device also senses gripping in one aspect.

The pen-like device is viewed by two or more cameras of known parameters to localize the fiducial markers in three dimensions and to infer the three-dimensional pose of the finger piece. The fiducial markers can be implemented, for example, as 1) retro-reflective spheres with illumination close to the camera; 2) concave or convex half spheres with illumination close to the camera; or 3) active markers such as a (blinking) LED. In one aspect, near infrared illumination of the finger piece is used, and filters are used to block the visible spectrum at the camera to minimize the distraction from background clutter.

Figure 5:
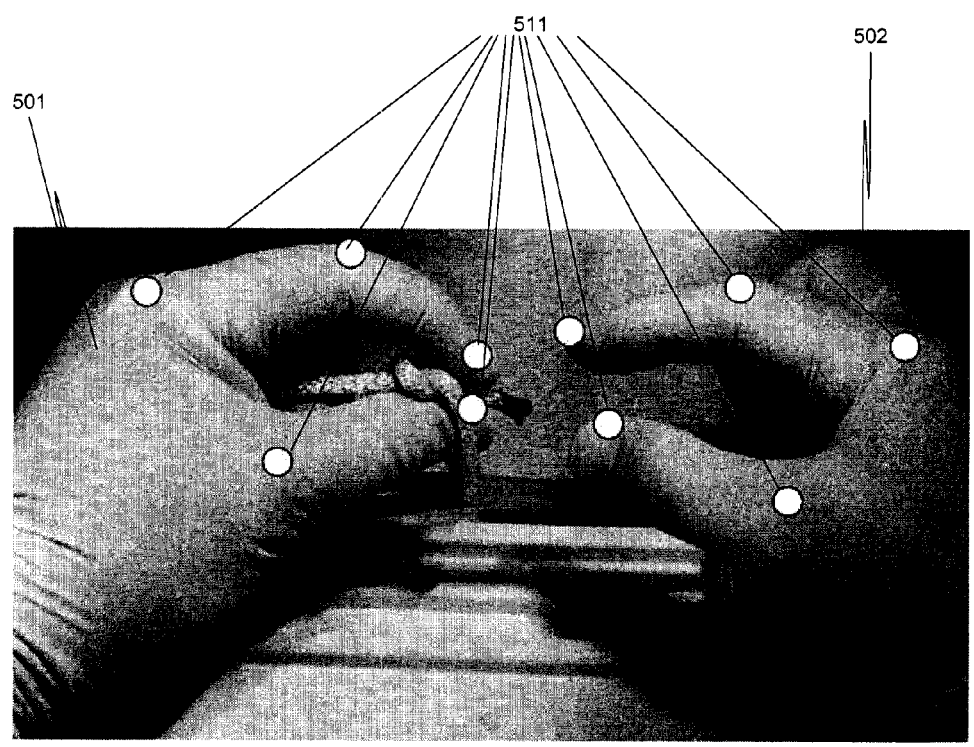
FIG. 5 is an illustration of placement of fiducial markers for hand tracking in a camera-based tracking system.

In another aspect, a data glove 501 (FIG. 5) or bare hand 502 is used, and fiducial markers 511 are attached to the thumb and index finger of glove 501 (and/or to other digits of the glove) that the surgeon is going to wear and/or directly to the skin of hand 502. Again, redundant markers can be used to accommodate self-occlusion. Fiducial markers also can be placed on other fingers to enable more user interface features through specifically defined hand gestures.

The three-dimensional locations of the fiducial markers are computed by triangulation of multiple cameras having a common field of view. The three-dimensional locations of the fiducial markers are used to infer the three-dimensional pose (translation and orientation) of the hand and also the grip size.

The marker locations need to be calibrated before use. For example, the surgeon can show the hand with markers in different poses to the camera. The different poses are then used in the calibration.

In yet another aspect, marker-less hand tracking is used. Articulated hand motion can be tracked by using images viewed from one or more cameras and processing these images via executing computer software. The executing computer software does not need to track all the degrees of freedom of the hand to be useful. The executing software only needs to track the part related to the two digits of a hand to be useful for controlling a surgical tool as demonstrated herein.

In camera based tracking, the accuracy of the measurements depends on the localization accuracy of the markers in the image; three-dimensional reconstruction accuracy due to camera geometry; and redundant data such as more than a minimal number, e.g., three, of fiducial markers, more than a minimal number (one or two) of cameras, and temporal averaging and filtering.

The three-dimensional reconstruction accuracy relies heavily on the accuracy of camera calibration. Some fiducial markers attached to known locations on the surgeon's console can be used to determine the extrinsic parameters (rotation and translation) of multiple cameras with respect to the surgeon's console. This process can be done automatically. Active fiducial markers can be used for the calibration fiducial markers since such markers are only turned on during a calibration process and before the procedure. During the procedure, the calibration fiducial markers are turned off to avoid confusion with the fiducial markers used to localize the surgeon's hands. The relative extrinsic parameters can also be computed by observing a moving marker in the common field of view of the cameras.

Other tracking technologies that are suitable for use include, but are not limited to, inertial tracking, depth camera tracking, and fiber bend sensing.

As used herein, a sensor element, sometimes called a tracking sensor, can be a sensor for any of the hand tracking technologies described above, e.g., a passive electromagnetic sensor, a fiducial marker, or a sensor for any of the other technologies.

Coordinate Systems

Prior to considering the various processes described above in further detail, one example of a surgeon's console 185B (FIG. 6A) is considered, and various coordinate systems are defined for use in the following examples. Surgeon's console 185B is an example of surgeon's console 185. Surgeon's console 185B includes a three-dimensional viewer 610, sometimes referred to as viewer 610, master tool manipulators 620L, 620R with master tool grips 621L, 621R, and a base 630. Master tool grip 621 (FIG. 6B) is a more detailed diagram of master tool grips 621L, 621R.

Master tool grips 621L, 621R of master tool manipulators 620L, 620R are held by surgeon 180B using the forefinger and thumb, so that targeting and grasping involves intuitive pointing and pinching motions. Master tool manipulators 620L, 620R in combination with master tool grips 621L, 621R are used to control teleoperated slave surgical instruments, teleoperated endoscopes, etc. in the same manner as known master tool manipulators in a known minimally invasive teleoperated surgical system. Also, the position coordinates of master tool manipulators 620L, 620R and master tool grips 621L, 621R are known from the kinematics used in controlling the slave surgical instruments.

In the normal viewing mode of operation, viewer 610 displays three-dimensional images of surgical site 103 from stereoscopic endoscope 112. Viewer 610 is positioned on console 185B (FIG. 6B) near the surgeon's hands so that the image of the surgical site seen in viewer 610 is oriented so that surgeon 180B feels that he or she is actually looking directly down onto surgical site 103. The surgical instruments in the image appear to be located substantially where the surgeon's hands are located and oriented substantially as surgeon 180B would expect based on the position of his hands. However, surgeon 180B can see neither his or her hands, nor the position or orientation of master tool grips 621L, 621R, while viewing the displayed image of the surgical site in viewer 610.

In one aspect, master tool manipulators 620L, 620R are moved from directly in front of surgeon 180B and under viewer 610 so that they are positioned over base 630, and so that they are no longer positioned under viewer 610, i.e., the master tool manipulators are parked out of the way of the hand gesture. This provides an unobstructed volume under viewer 610 in which surgeon 180B can make hand gestures, either or both of hand gesture poses or hand gesture trajectories.

In the aspect of FIG. 6A, three coordinate systems are defined with respect to surgeon's console 185B: a view coordinate system 660, a world coordinate system 670, and a tracker coordinate system 650. Note equivalent coordinate systems are defined for surgeon 181 (FIG. 1), so that the mapping described more completely below can be done for tracking data from master finger tracking grip 170 or from master tool grips 621L, 621R. See for example, U.S. patent application Ser. No. 12/617,937 (filed 13 Nov. 2009, disclosing "Patient-Side Surgeon Interface For a Minimally Invasive Teleoperated Surgical Instrument"), which was previously incorporated by reference.

In view coordinate system 660, surgeon 180B is looking down Z-axis Zview. Y-axis Yview points upward in the display. X-axis Xview points to the left in the display. In world coordinate system 670, Z-axis Zworld is a vertical axis. World X-axis Xworld and world Y-axis Yworld are in a plane perpendicular to Z-axis Zworld.

Figure 6B:
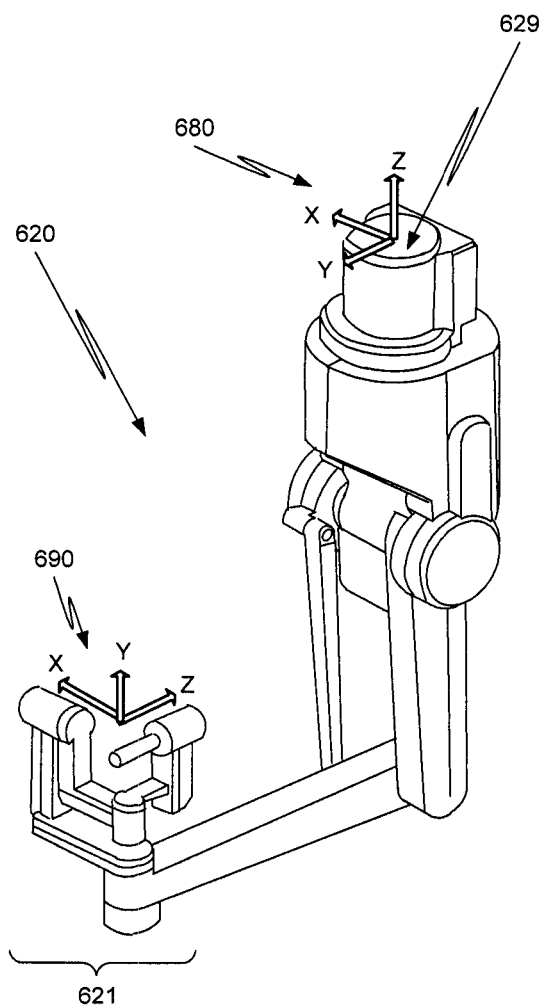

FIG. 6B is a more detailed illustration of master tool grip 621 and master tool manipulators 620. Coordinate systems 680, 690 are discussed more completely below with respect to method 1100 of FIG. 11.

Process of Surgical Instrument Control via Hand Tracking

Figure 7:
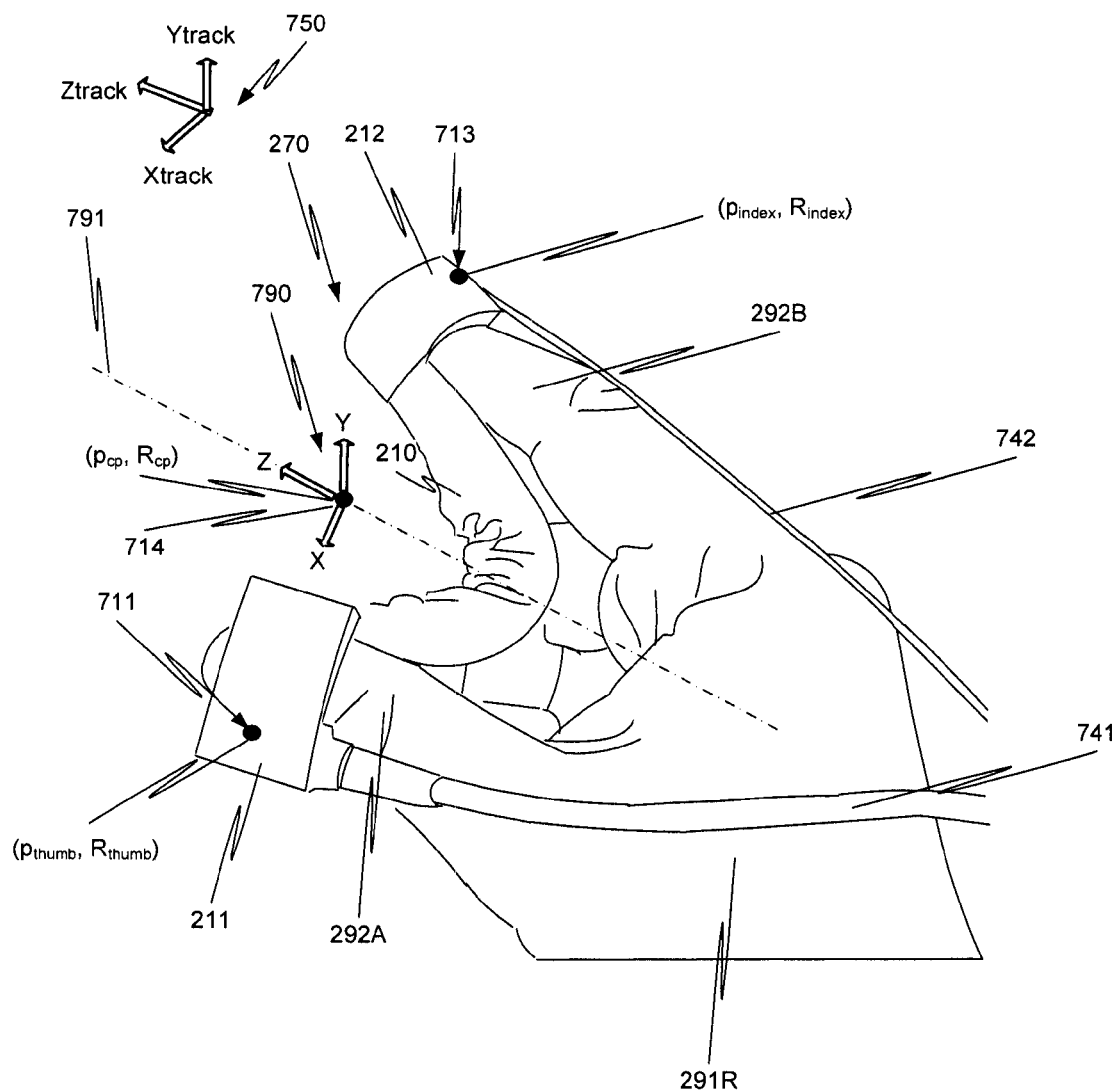
FIG. 7 is a more detailed illustration of a hand-worn master tool grip and the locations and coordinate systems used in hand tracking by the minimally invasive teleoperated surgical system of FIG. 1.

FIG. 7 is an illustration of sensor 212 mounted on forefinger 292B with a location 713 in tracking coordinate system 750, and a sensor 211 mounted on thumb 292A with a location 711 in tracking coordinate system 750. Sensors 211 and 212 are part of the electromagnetic tracking system described above. Thumb 292A and index finger 292B are examples of digits of right hand 291R. As noted previously, a part of a human hand includes at least one digit of the hand. As is known to those knowledgeable in the field, the fingers, sometimes called digits or phalanges, of the hand are the thumb (first digit), index finger (second digit; forefinger), middle finger (third digit), ring finger (fourth digit), and little finger (fifth digit).

Herein, the thumb and index finger are used as examples of two digits of a human hand. This is illustrative only and is not intended to be limiting. For example, the thumb and the middle finger could be used in place of the thumb and index finger. The description herein is directly applicable to the use of the middle finger also. Also, the use of the right hand is illustrative only. When similar sensors are worn on the left hand, the description herein is directly applicable to the left hand also.

A cable 741, 742 connects sensors 211, 212 of master finger tracking grip 270 to hand tracking controller 130. In one aspect, cable 741, 742 carries position and orientation information from sensors 211, 212 to hand tracking controller 130.

Use of a cable to transmit sensed position and orientation data to hand tracking controller 130 is illustrative only and is not intended to be limiting to this specific aspect. In view of this disclosure one knowledgeable in the field can select a mechanism to transmit sensed position and orientation data from the master finger tracking grip or master finger tracking grips to hand tracking controller 130 (e.g., by use of wireless connection).

Cable 741, 742 does not inhibit motion of master finger tracking grip 270. Since master finger tracking grip 270 is mechanically ungrounded, each master finger tracking grip is effectively unconstrained for both position and orientation motions within the surgeon's reachable workspace and the hand-tracking transmitter's workspace (e.g., left-right, up-down, in-out, roll, pitch, and yaw in a Cartesian coordinate system).

In one aspect, as described above, each sensor 211, 212 on master finger tracking grip 270 senses three degrees of translation and three degrees of rotation, i.e., six degrees of freedom. Thus, the sensed data from the two sensors represents twelve degrees of freedom. In another aspect, each sensor 211, 212 on master finger tracking grip 270 senses three degrees of translation and two degrees of rotation (yaw and pitch), i.e., five degrees of freedom. Thus, the sensed data from the two sensors represents ten degrees of freedom.

Using a control point position and control point orientation based on the tracked locations to control a teleoperated slave surgical instrument requires six degrees of freedom (three translation and three orientation), as described more completely below. Thus, in the aspects where each sensor has five or six degrees of freedom, sensors 211, 212 provide redundant degrees of freedom. As described above and more completely below, the redundant degrees of freedom are mapped to parameters used to control teleoperated slave surgical instrument aspects other than position and orientation.

In yet a further aspect, each sensor 211, 212 senses only three translation degrees of freedom and so together represent six degrees of freedom. This is sufficient to control three degrees of translation, roll, and grip closure of a slave surgical instrument that does not include a wrist mechanism. The following description is used to generate the control point location using the six degrees of freedom. The control point orientation is taken as the orientation of the slave surgical instrument. The grip closure parameter is determined as described below using the control point location and the control point orientation. The roll is determined as described above using the relative motion of the thumb and index finger.

In either the aspect where the sensors sense six degrees of freedom, or where the sensors sense five degrees of freedom, index finger sensor 212 generates a signal representing an index finger position $p_{index}$ and an index finger orientation $R_{index}$ in tracking coordinate frame 750. Thumb sensor 211 generates a signal representing a thumb position $p_{thumb}$ and a thumb orientation $R_{thumb}$ in tracking coordinate frame 750. In one aspect, positions $p_{index}$ and $p_{thumb}$ are taken as aligned with the center of the user's fingernail on index finger 292B and the center of the user's thumbnail on thumb 292A, respectively.

In this example, positions $p_{index}$ and $p_{thumb}$ are each represented as a three-by-one vector in tracking coordinate frame 750. Positions $p_{index}$ and $p_{thumb}$ are in tracker coordinates.

Orientations $R_{index}$ and $R_{thumb}$ are each represented as a three-by-three matrix in tracking coordinate frame 750, i.e., $$R_{index} = \begin{bmatrix} R_{index11} & R_{index12} & R_{index13} \\ R_{index21} & R_{index22} & R_{index23} \\ R_{index31} & R_{index31} & R_{index33} \end{bmatrix}$$

$$R_{thumb} = \begin{bmatrix} R_{thumb11} & R_{thumb12} & R_{thumb13} \\ R_{thumb21} & R_{thumb22} & R_{thumb23} \\ R_{thumb31} & R_{thumb31} & R_{thumb33} \end{bmatrix}$$

A control point position $p_{cp}$ is centered between index finger 292B and thumb 292A. Control point position $p_{cp}$ is in control point frame 790, but is specified in tracker coordinates. The Z-axis of control point frame 790 extends through control point position $p_{cp}$ in the pointing direction, as described more completely below.

Also, as explained below, index finger 292B and thumb 292A are mapped to the jaws of a slave surgical instrument, but the two digits are more dexterous than the instrument jaws. The Y-axis of control point frame 790 corresponds to the pin used for instrument jaw closure. Thus, the Y-axis of control point frame 790 is perpendicular to a vector between index finger 292B and thumb 292A, as described below.

Control point position $p_{cp}$ is represented as a three-by-one vector in tracker coordinates of tracking coordinate frame 750. Control point orientation $R_{cp}$ is represented as a three-by-three matrix in tracker coordinates, i.e., $$R_{cp} = \begin{bmatrix} R_{cp11} & R_{cp12} & R_{cp13} \\ R_{cp21} & R_{cp22} & R_{cp23} \\ R_{cp31} & R_{cp31} & R_{cp33} \end{bmatrix}$$

Figure 8:
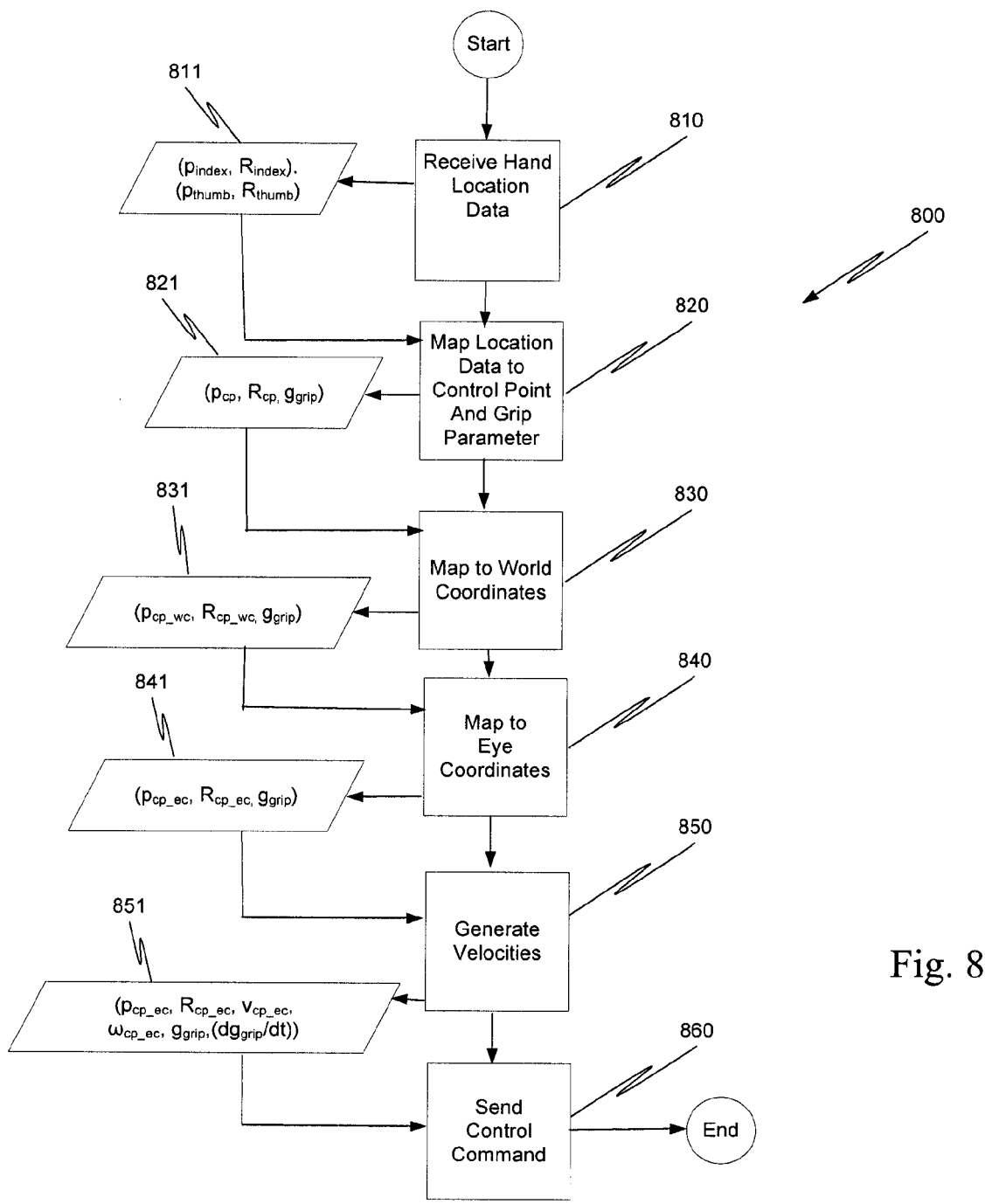
FIG. 8 is a process flow diagram of a process used in the tracking system to track digits of the hand and used to generate data for teleoperation of a slave surgical instrument in the minimally invasive teleoperated surgical system of FIG. 1

FIG. 8 is a process flow diagram for mapping a location of part of a hand to a grip closure parameter used to control the grip of a slave surgical instrument, e.g., one of the teleoperated slave surgical instruments in FIG. 1. This mapping also maps a temporal change in the location to a new grip closure parameter and a corresponding location of a slave instrument tip and the velocity in moving to that location.

Initially, upon entry to process 800, RECEIVE HAND LOCATION DATA process 810 receives index finger position and orientation ($p_{index}$, $R_{index}$) and thumb position and orientation ($p_{thumb}$, $R_{thumb}$), which in this example are stored as data 811. Index finger position and orientation ($p_{index}$, $R_{index}$) and thumb position and orientation ($p_{thumb}$, $R_{thumb}$) are based on data from the tracking system. Process 810 transfers to MAP LOCATION DATA TO CONTROL POINT AND GRIP PARAMETER process 820.

MAP LOCATION DATA TO CONTROL POINT AND GRIP PARAMETER process 820 generates a control point position $p_{cp}$, a control point orientation $R_{cp}$, and a grip closure parameter $g_{grip}$ using index finger position and orientation ($p_{index}$, $R_{index}$) and thumb position and orientation ($p_{thumb}$, $R_{thumb}$). Control point position $p_{cp}$, control point orientation $R_{cp}$, and grip closure parameter $g_{grip}$ are stored as data 821.

In one aspect, the control point mapping performed in process 820 is defined to emulate key properties of the known master tool manipulators control point placement. Thus, the response to thumb and index finger motion will be familiar and intuitive to users of the known teleoperated minimally invasive surgical system with a surgeon's console similar to surgeon's console 180B (FIG. 6A).

Figure 9:
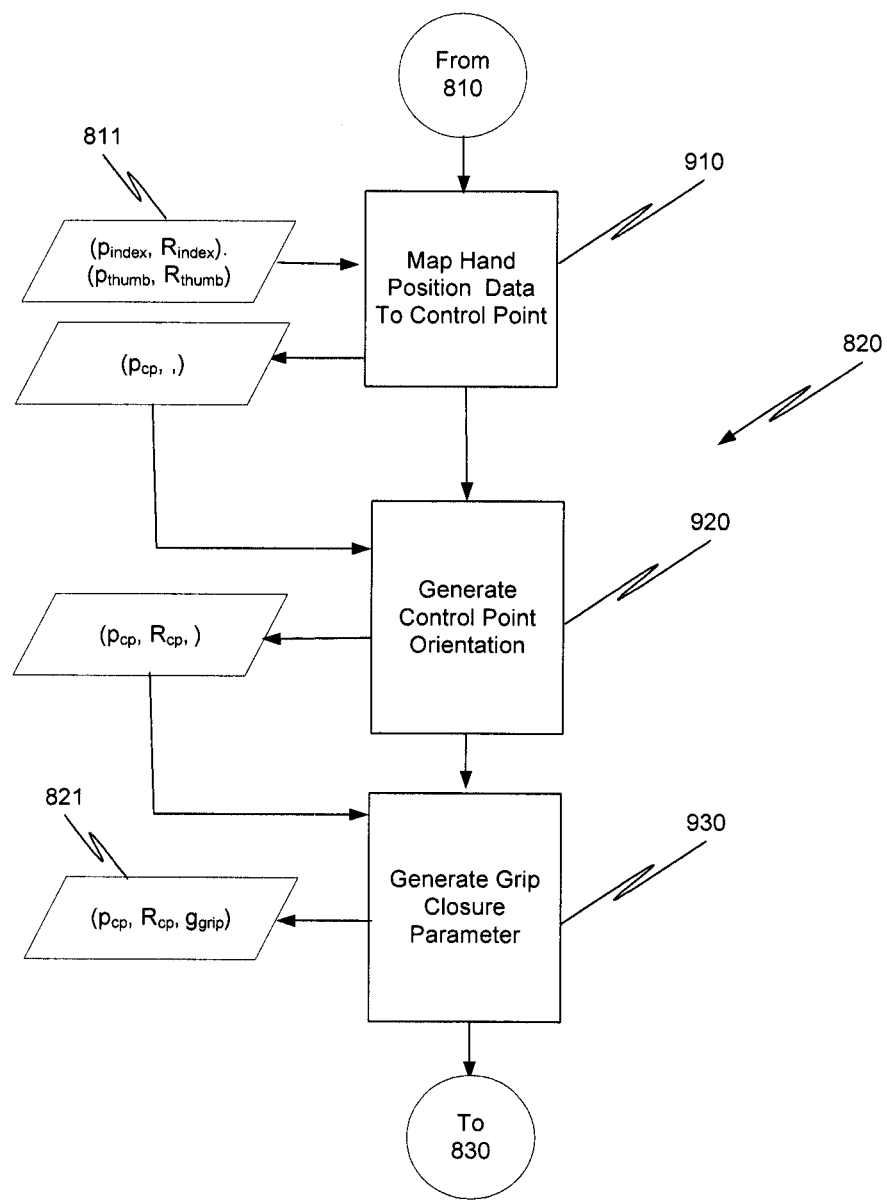
FIG. 9 is a more detailed process flow diagram of the MAP LOCATION DATA TO CONTROL POINT AND GRIP PARAMETER process of FIG. 8.

FIG. 9 is a more detailed process flow diagram for one aspect of MAP LOCATION DATA TO CONTROL POINT AND GRIP PARAMETER process 820. First, in process 820, MAP HAND POSITION DATA TO CONTROL POINT process 910 generates a location of control point position $p_{cp}$ from index finger position $p_{index}$ and thumb position $p_{thumb}$, i.e., $$p_{cp} = 0.5*(p_{thumb} + p_{index})$$

Control point position $p_{cp}$ is the average of finger position $p_{index}$ and thumb position $p_{thumb}$. MAP HAND POSITION DATA TO CONTROL POINT process 910 transfers processing to GENERATE CONTROL POINT ORIENTATION process 920.

As indicated above, the Z-axis of the control point orientation is aligned in the pointing direction. In this aspect of GENERATE CONTROL POINT ORIENTATION process 920, the Rodriquez axis/angle formula is used to define the Z-axis pointing direction vector $\hat{z}_{half}$ for the control point orientation as a half rotation between index finger pointing direction vector $\hat{z}_{index}$ and thumb pointing direction vector $\hat{z}_{thumb}$. From thumb orientation $R_{thumb}$, thumb pointing direction vector $\hat{z}_{thumb}$ is:

$$\hat{z}_{thumb} = [R_{thumb13} \; R_{thumb23} \; R_{thumb33}]'$$

Similarly, from index finger orientation $R_{index}$, index finger pointing direction vector $\hat{z}_{index}$ is:

$$\hat{z}_{index} = [R_{index13} \; R_{index23} \; R_{index33}]'$$

Vector $\omega$ is a vector perpendicular to index finger pointing direction vector $\hat{z}_{index}$ and thumb pointing direction vector $\hat{z}_{thumb}$. Vector $\omega$ is defined as the cross product of index finger pointing direction vector $\hat{z}_{index}$ and thumb pointing direction vector $\hat{z}_{thumb}$, i.e., $$\omega = \hat{z}_{index} \times \hat{z}_{thumb}$$

Angle $\theta$ is the magnitude of the angle between index finger pointing direction vector $\hat{z}_{index}$ and thumb pointing direction vector $\hat{z}_{thumb}$. Angle $\theta$ is defined as, $$\theta = \begin{cases} \sin^{-1}(\|\omega\|) & \text{if } \|\omega\| < 1 \\ \sin^{-1}(1) & \text{otherwise} \end{cases}$$

With axis $\omega$ and angle $\theta$, Z-axis pointing direction vector $\hat{z}_{half}$ is:

$$\hat{z}_{half} = R\left(\omega, \frac{\theta}{2}\right) * \hat{z}_{index}$$

Thus, process 910 has generated control point position $p_{cp}$ and the initial part of process 920 has generated the approximate pointing direction of the Z-axis in control point frame 790. One could proceed to interpolate index finger and thumb orientation vectors to generate control point unit vector axes $\hat{x}_{cp}$ and $\hat{y}_{cp}$ in a similar manner and then re-orthogonalize them to produce a control point orientation matrix.

However, greater teleoperation dexterity can be achieved from the tracked locations of the digits by using the following mapping. This mapping uses the relative positions of the index finger and thumb to effectively roll and yaw the control point as if manipulating a small gimbal between the fingers. The remainder of process 920 is performed as follows to generate a complete set of orthonormal control point unit vectors axes $\hat{x}_{cp}$, $\hat{y}_{cp}$, and $\hat{z}_{cp}$.

$$\hat{x}_{cp} = \frac{p_{index} - p_{thumb}}{\|p_{index} - p_{thumb}\|}$$

$$\hat{y}_{cp} = \hat{z}_{half} \times \hat{x}_{cp}$$

$$\hat{z}_{cp} = \hat{x}_{cp} \times \hat{y}_{cp}$$

With these vectors, control point orientation $R_{cp}$ is:

$$R_{cp} = [\hat{x}_{cp} \; \hat{y}_{cp} \; \hat{z}_{cp}] = \begin{bmatrix} R_{cp11} & R_{cp12} & R_{cp13} \\ R_{cp21} & R_{cp22} & R_{cp23} \\ R_{cp31} & R_{cp31} & R_{cp33} \end{bmatrix}$$

Now with processes 910 and 920, process 820 has mapped index finger and thumb positions and orientations ($p_{index}$, $R_{index}$), ($p_{thumb}$, $R_{thumb}$) to control point position and orientation ($p_{cp}$, $R_{cp}$). Process 820 must still generate grip closure parameter $g_{grip}$. Thus, GENERATE CONTROL POINT ORIENTATION process 920 transfers processing to GENERATE GRIP CLOSURE PARAMETER process 930.

In process 930, grip closure is determined by the distances of index finger position $p_{index}$ and thumb position $p_{thumb}$ from the centerline axis defined by control point position $p_{cp}$ and Z-axis direction $\hat{z}_{cp}$. This allows grip closure to be invariant to sliding when the thumb and forefinger are touching.

Thus, index finger position $p_{index}$ and thumb position $p_{thumb}$ are mapped onto the Z-axis in frame 790. Position $p_{index\_proj}$ is the projection of index finger position $p_{index}$ onto the Z-axis of frame 790, and position $p_{thumb\_proj}$ is the projection of thumb position $p_{thumb}$ onto the Z-axis of frame 790.

$$p_{index\_proj} = p_{cp} + (\hat{z}_{cp} \cdot (p_{index} - p_{cp})) * \hat{z}_{cp}$$

$$p_{thumb\_proj} = p_{cp} + (\hat{z}_{cp} \cdot (p_{thumb} - p_{cp})) * \hat{z}_{cp}$$

Position $p_{index\_proj}$ and position $p_{thumb\_proj}$ are used to evaluate an evaluation grip closure distance $d_{val}$, i.e., $$d_{val} = \|p_{index} - p_{index\_proj}\| + \|p_{thumb} - p_{thumb\_proj}\|$$

Herein, the double parallel lines are the known representative of the two-norm Euclidean distance. Evaluation grip closure distance $d_{val}$ is bounded by a maximum distance threshold $d_{max}$ and a minimum distance threshold $d_{min}$. As illustrated in FIG. 7, padded foam connector 210 between sensors 211, 212 constrains the digits to be within a fixed separation, i.e., between a maximum distance threshold $d_{max}$ and a minimum distance threshold $d_{min}$. Additionally, a neutral distance $d_0$ corresponds to the separation distance when the two digits are just touching.

For a particular set of sensors and a connector, a maximum distance threshold $d_{max}$, a minimum distance threshold $d_{min}$, and neutral distance $d_0$ are empirically determined. In one aspect, three different combinations of sensors and a connector are provided for small, average, and large hands. Each combination has its own maximum distance threshold $d_{max}$, minimum distance threshold $d_{min}$, and neutral distance $d_0$ as the length of connector 210 is different in each of the combinations.

Process 930 compares distance $d_{val}$ to minimum distance threshold $d_{min}$. If the comparison finds that distance $d_{val}$ is less than minimum distance threshold $d_{min}$, grip closure distance d is set to minimum threshold distance $d_{min}$. Otherwise, process 930 compares distance $d_{val}$ to maximum distance threshold $d_{max}$. If the comparison finds that distance $d_{val}$ is greater than maximum distance threshold $d_{max}$, grip closure distance d is set to maximum threshold distance dmax. Otherwise, grip closure distance d is set to distance $d_{val}$.

The testing performed on distance $d_{val}$ to determine grip closure distance d is summarized as:

$$d = \begin{cases} d_{min} & d_{val} < d_{min} \\ d_{max} & d_{val} > d_{max} \\ d_{val} & \text{otherwise} \end{cases}$$

Next in process 930, grip closure parameter $g_{grip}$ is generated:

$$g_{grip} = \begin{cases} \frac{d - d_0}{d_{max} - d_0} & d > d_0 \\ \frac{d - d_{min}}{d_0 - d_{min}} & \text{otherwise} \end{cases}.$$

Thus, a grip closure distance d between maximum distance threshold $d_{max}$ and distance $d_0$ is mapped to a value between zero and one. A grip closure distance d between minimum distance threshold $d_{min}$ and distance $d_0$ is mapped to a value between minus one and zero.

A value of one for grip closure parameter $g_{grip}$ is obtained when index finger 292B and thumb 292A are separated to the maximum extent permitted by connector 210 (FIG. 2A). A value of zero for grip closure parameter $g_{grip}$ is obtained when the tip of index finger 292B and the tip of thumb 292A are just touching (FIG. 2C). Values in a range between zero and one control the opening/closing of the jaws of the end effector of a slave surgical instrument. A value of minus one for grip closure parameter $g_{grip}$ is obtained when index finger 292B and thumb 292A are touching and connector 210 is fully compressed between index finger 292B and thumb 292A (FIG. 2D). Values in a range between zero and minus one control the jaw force of the closed jaws of the end effector. Connector 210 provides a passive haptic cue for jaw closure.

This example of mapping grip closure distance d to a value in one of two ranges is illustrative only and is not intended to be limiting. The example is illustrative of mapping grip closure distance d to a value in a first range of grip closure parameter $g_{grip}$ to control the opening/closing of jaws of an end effector of a slave surgical instrument when grip closure distance d is greater than neutral distance $d_0$. Here "opening/closing" means the opening and closing of the jaws. Grip closure distance d is mapped to a value in a second range of the grip closure parameter $g_{grip}$ to control jaw force of the closed jaws of the end effector when grip closure distance d is less than neutral distance $d_0$.

Thus, process 820 has mapped index finger position and orientation ($p_{index}$, $R_{index}$) and thumb position and orientation ($p_{thumb}$, $R_{thumb}$) into a control point position and orientation ($p_{cp}$, $R_{cp}$) and grip closure parameter $g_{grip}$ that is stored as data 821. Process 820 transfers to MAP TO WORLD COORDINATES process 830 (FIG. 8).

MAP TO WORLD COORDINATES process 830 receives data 821, and maps data 821 to a world coordinate system. (See world coordinate system 670 (FIG. 6A). Specifically, control point position and orientation ($p_{cp}$, $R_{cp}$) and grip closure parameter $g_{grip}$ are mapped to world coordinates control point position and orientation ($p_{cp\_wc}$, $R_{cp\_wc}$) using a four by four homogeneous transform $^{wc}T_{tc}$ that maps coordinates in tracker coordinate system 750 (FIG. 7B) to coordinates in world coordinate system 670, e.g., $$^{wc}T_{tc} = \begin{bmatrix} ^{wc}R_{tc} & ^{wc}t_{tc} \\ 0 & 1 \end{bmatrix}$$

where
$^{wc}R_{tc}$ maps an orientation in tracker coordinates tc to an orientation in world coordinates wc, and
$^{wc}t_{tc}$ translates a position in tracker coordinates tc to a position in world coordinates wc.

Grip closure parameter $g_{grip}$ is not changed by this mapping. The data in world coordinates wc is stored as data 831. Process 830 transfers to MAP TO EYE COORDINATES process 840.

MAP TO EYE COORDINATES process 840 receives data 831 in world coordinates wc and maps data 831 to an eye coordinate system (See eye coordinate system 660 (FIG. 6A). Specifically, world coordinates control point position and orientation ($p_{cp\_wc}$, $R_{cp\_wc}$) and grip closure parameter $g_{grip}$ are mapped to eye coordinates control point position and orientation ($p_{cp\_ec}$, $R_{cp\_ec}$) using a four by four homogeneous transform $^{ec}T_{wc}$ that maps coordinates in world coordinate system 670 (FIG. 6A) to coordinates in eye coordinate system 660, e.g., $$^{ec}T_{wc} = \begin{bmatrix} ^{ec}R_{we} & ^{ec}t_{wc} \\ 0 & 1 \end{bmatrix}$$

where
$^{ec}R_{wc}$ maps an orientation in world coordinates wc to an orientation in eye coordinates ec, and
$^{ec}t_{wc}$ is a translation of a position in world coordinates wc to a position in eye coordinates ec.

Again, grip closure parameter $g_{grip}$ is not changed by the mapping. The data in eye coordinates is stored as data 841. Process 840 transfers to GENERATE VELOCITIES process 850.

In process 800, mapping processes 830 and 840 are described as two different processes for ease of illustration only. In one aspect, mapping processes 830 and 840 are combined so that the control point data in tracker coordinates tc is mapped directly to data in eye coordinates ec using a four by four homogeneous transform $^{ec}T_{tc}$ that maps coordinates in tracker coordinate system 650 (FIG. 6A) to coordinates in eye coordinate system 660, e.g., $$^{ec}T_{tc} = \begin{bmatrix} ^{ec}R_{we}{}^{wc}R_{tc} & (^{ec}R_{wc}{}^{wc}t_{tc} + {}^{ec}t_{wc}) \\ 0 & 1 \end{bmatrix}.$$

In this aspect, the position of the control point in eye coordinates $p_{cp\_ec}$ is:

$$p_{cp\_ec} = {}^{ec}T_{tc}p_{cp\_tc},$$

and the orientation of the control point in eye coordinates $R_{cp\_ec}$ is:

$$R_{cp\_ec} = {}^{ec}R_{wc}{}^{wc}R_{tc}R_{cp\_tc}$$

In some aspects, the world coordinate mapping may be eliminated. In this case, the control point data is mapped directly from the tracking coordinate system into the eye coordinate system without utilizing a world coordinate system.

For teleoperation, position, orientation, and velocity are needed. Thus, GENERATE VELOCITIES process 850 generates the needed velocities. The velocities can be generated in a number of ways. Some implementations, such as inertial and gyroscope sensors, can directly measure differential signals to produce a linear velocity and an angular velocity of the control point. If the velocities cannot be directly measured, process 850 estimates the velocities from the location measurements in the eye coordinate system in one aspect.

The velocities may be estimated using finite differences in the eye coordinate system over the sampling interval. For example, linear velocity $v_{cp\_ec}$ is estimated as:

$$v_{cp\_ec} = \frac{p_{cp\_ec}(t1) - p_{cp\_ec}(t0)}{\Delta t}$$

and angular velocity $\omega_{cp\_ec}$ is estimated as:

$$R_\Delta = R_{cp\_ec}(t0)' * R_{cp\_ec}(t1)$$

$$\omega_\Delta = 0.5 * \begin{bmatrix} R_{\Delta 32} - R_{\Delta 23} \\ R_{\Delta 13} - R_{\Delta 31} \\ R_{\Delta 21} - R_{\Delta 12} \end{bmatrix}$$

$$\omega_{cp\_ec} = \frac{Rcp\_ec(t0) * \omega_\Delta}{\Delta t}$$

In another aspect of GENERATE VELOCITIES process 850, control point linear velocity $v_{cp\_tc}$ and control point angular velocity $\omega_{cp\_tc}$ are sensed in tracker coordinates of tracker coordinate system 750 (FIG. 7). In this aspect, directly sensed control point linear velocity $v_{cp\_tc}$ and directly sensed control point angular velocity $\omega_{cp\_tc}$ are rotated from tracker coordinate system 750 to eye coordinate system 660 using a rotation $^{ec}R_{tc}$. Specifically, using the rotation mappings as defined above, $$^{ec}R_{tc} = {}^{ec}R_{wc}{}^{wc}R_{tc}$$

$$v_{cp\_ec} = {}^{ec}R_{tc}v_{cp\_tc}$$

$$\omega_{cp\_ec} = {}^{ec}R_{tc}\omega_{cp\_tc}$$

GENERATE VELOCITIES process 850 transfers to SEND CONTROL COMMAND process 860. Process 860 sends an appropriate system control command to the slave surgical instrument based upon the position, orientation, velocities, and grip closure parameter stored as data 851.

In one aspect, processes 810 to 850 are performed by hand tracking controller 130 (FIG. 1). Controller 130 executes finger tracking module 135 on a processor 131 to perform processes 810 to 850. In this aspect, finger tracking module 135 is stored in memory 132. Process 850 sends a system event to system controller 140 that in turn performs process 860.

It is to be appreciated that hand tracking controller 130 and system controller 140 may be implemented in practice by any combination of hardware, software that is executed on a processor, and firmware. Also, functions of these controllers, as described herein, may be performed by one unit, or divided up among different components, each of which may be implemented in turn by any combination of hardware, software that is executed on a processor, and firmware. When divided up among different components, the components may be centralized in one location or distributed across system 100 for distributed processing purposes.

Process of Gesture Hand Pose and Gesture Trajectory Control

Figure 10:
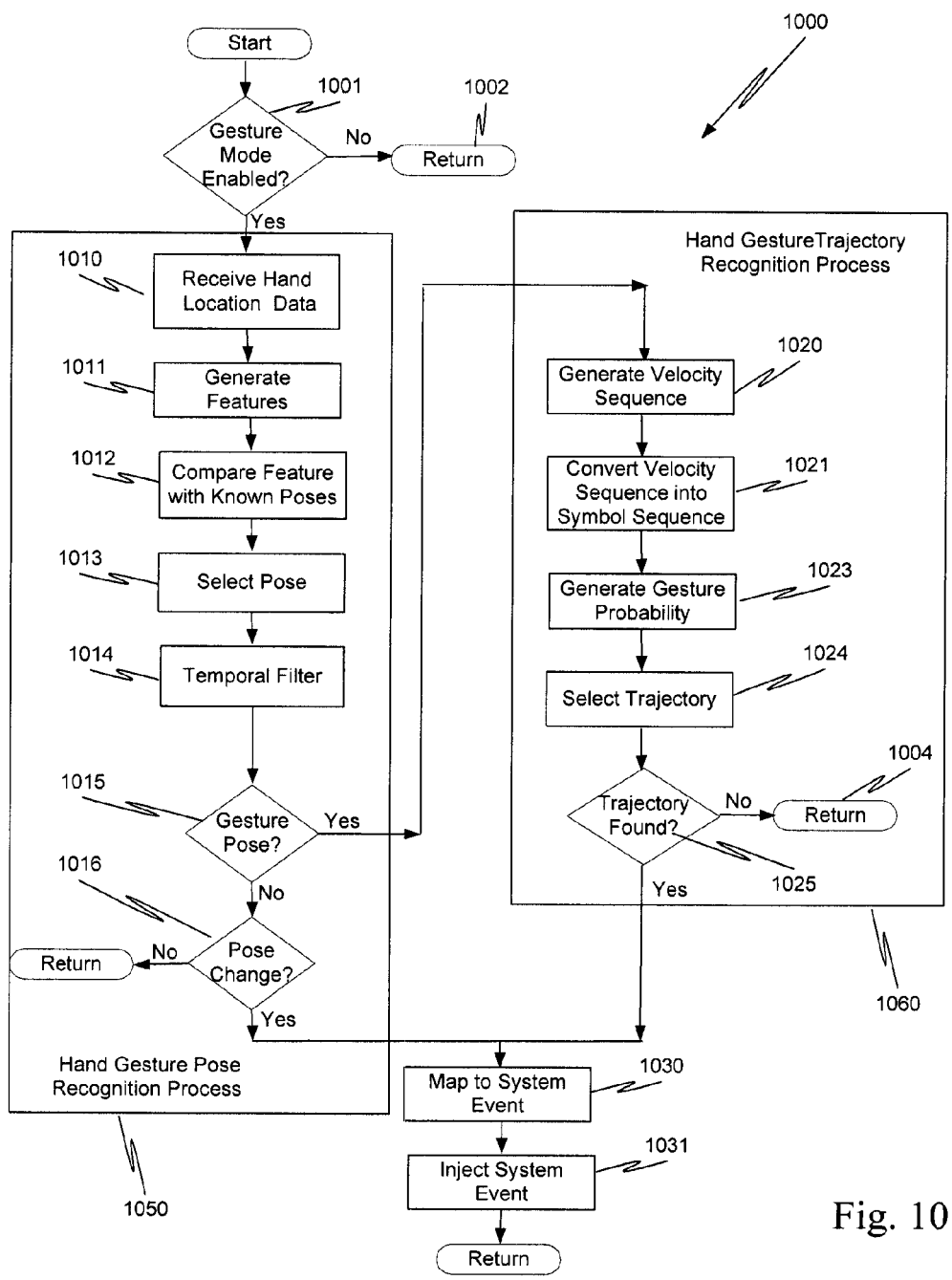
FIG. 10 is a process flow diagram of a process used in the tracking system to recognize hand gesture poses and hand gesture trajectories.

FIG. 10 is a process flow diagram of one aspect of a process 1000 of hand gesture pose and hand gesture trajectory control of system 100. In one aspect as described above, a hand gesture pose recognition process 1050 uses a multi-dimensional Bayesian classifier and a hand gesture trajectory recognition process 1060 uses a discrete Hidden Markov Model Λ.

As described above, FIGS. 3A to 3D are examples of hand gesture poses. To train hand gesture pose recognition process 1050, a number of hand gesture poses are specified. The number of hand gesture poses utilized is limited by the ability to define unique poses that can unambiguously be identified by recognition process 1050, and by the ability of the surgeon to remember and reliably reproduce each of the different hand gesture poses.

In addition to defining the hand gesture poses, a feature set including a plurality of features $f_i$, where i ranges from 1 to n, is defined. Number n is the number of features used. The number of and type of features is selected so that each of the hand gesture poses in the set of permissible poses can be accurately identified. In one aspect, number n is six.

The following is an example of one feature set with n features.

$$f_1 = \hat{z}_{index} \cdot \hat{z}_{thumb}$$

$$f_2 = \|p_{thumb} - p_{index}\|$$

$$f_3 = (p_{thumb} - P_{index}) \cdot \hat{z}_{index}$$

$$f_4 = \|p_{thumb} - p_{index} + f_3 * \hat{z}_{index}\|$$

$$f_5 = \hat{z}_{thumb} \cdot [0\ 0\ 1]$$

...

$$f_n = \hat{x}_{thumb} \cdot \hat{z}_{index}$$

Feature $f_1$ is the dot product of pointing direction of $\hat{z}_{index}$ index finger 292B and pointing direction $\hat{z}_{thumb}$ of thumb 292A. Feature $f_2$ is the distance between index finger 292B and thumb 292A. Feature $f_3$ is the distance of thumb 292A projected on pointing direction $\hat{z}_{index}$ of index finger 292B. Feature $f_4$ is the distance of thumb 292A from the axis along pointing direction $\hat{z}_{index}$ of index finger 292B. Feature $f_5$ is the Z-component of pointing direction $\hat{z}_{thumb}$ of thumb 292A.

Feature $f_n$ is the dot product of thumb normal vector $\hat{x}_{thumb}$ of thumb 292A and pointing direction $\hat{z}_{index}$ of index finger 292B.

Prior to using method 1000, it is necessary to develop a training database of hand gesture poses. A number of different users produce each hand gesture pose at least one, and the position and orientation data for each hand gesture pose for each user is measured using the tracking system. For example, each person in a group of people makes each of the permissible hand gesture poses. Index finger and thumb positions and orientations ($P_{index}$, $R_{index}$), ($p_{thumb}$, $R_{thumb}$) are saved for each of the hand gesture poses for each person in the group in the training database.

Using the training database, a set of features $\{f_i\}$ is generated for each hand gesture pose for each user. The set of training feature vectors for each hand gesture pose is then used to compute, a mean $\bar{f}_i$ and a covariance $\Sigma_{fi}$.

Thus, the training database is used to obtain a feature vector mean and covariance for each trained gesture. In addition, for each hand gesture pose, a Mahalanobis distance $d(f_i)$ (See discussion below) is generated for each trainer and the maximum Mahalanobis distance $d(f_i)$ for each hand gesture pose is saved as a threshold for that hand gesture pose.

One can also use the Mahalanobis distance measure to verify that all trained gestures are sufficiently different and unambiguous for the given set of features used. This can be accomplished by testing the Mahalanobis distance of a given gesture's feature vector mean $\bar{f}_i$ and the feature vector means of all other permissible gesture poses. This test distance should be much larger than the maximum training distance threshold used for that given gesture.

As is known to those knowledgeable in the field, a specification of a Hidden Markov Model requires specification of two model parameters N, M and three probability measures A, B, $\pi$. Hidden Markov Model $\Lambda$ is represented as:

$$\Lambda = (A, B, \pi)$$

Model parameter N is the number of states in the model, and model parameter M is the number of observation symbols per state. The three probability measures are state transition probability distribution A, observation gesture probability distribution B, and initial state distribution $\pi$.

In one aspect for a discrete Hidden Markov Model, transition probability distribution A is an N×N matrix. Observation gesture probability distribution B is an N×M matrix, and initial state distribution $\pi$ is an N×1 matrix.

Given an observation sequence o and Hidden Markov Model $\Lambda$, the probability of observation sequence o given Hidden Markov Model $\Lambda$, i.e., P(o|$\Lambda$) is evaluated in process 1000, as described more completely below.

To generate the probability distributions for Hidden Markov Model $\Lambda$, a training database is needed. Prior to obtaining the training database, a set of hand gesture trajectories are specified.

A number of test subjects j are selected to make each of the hand gesture trajectories. While in FIG. 4C, the sixteen hand gesture trajectories are presented in a two-dimensional projected form, the test subjects are unconstrained when performing the various hand gesture trajectories, which allows for some three-dimensional variations to arise. In one aspect, each subject performed each hand gesture trajectory k times, this produces j*k training sequences per hand gesture trajectory.

In one aspect, a discrete left-right Hidden Markov Model was used. Hidden Markov Model $\Lambda$ was chosen such that probability P(o|$\Lambda$) is locally maximized using an iterative Baum-Welch method. See for example, Lawrence R. Rabiner, "*A Tutorial on Hidden Markov Models and Selected Applications in Speech Recognition*," Proceedings of the IEEE, Vol. 77, No. 2, pp. 257-286 (February 1989), which is incorporated herein by reference as a demonstration of knowledge of Hidden Markov Models of those knowledgeable in the models. In one aspect, the iterative method was stopped when the model converged within 0.1 percent for three successive iterations.

The initial state probability $\pi$ was set so that the model always starts with state one. Transition probability matrix A was initialized with random entries, which were sorted in descending order on a row-by-row basis. To enforce the left-to-right structure, all entries in the lower-diagonal of transition probability matrix A were set to zero. Furthermore, transitions greater than two states were disallowed by setting entries to zero where (i-j)>2 for all rows i and columns j. Transition probability matrix A was normalized at the end on a row-by-row basis.

The initialization for the observation probability matrix B partitioned the observation sequence uniformly based on the desired number of states. Therefore, each state can initially observe one or more symbols with a probability based on a local frequency count. This matrix was also normalized on a row-by-row basis. See for example, N. Liu, R. I. A. Davis, B. C. Lovell, P. J. Kootsookos, "*Effect of Initial HMM Choices in Multiple Sequence Training for Gesture Recognition*," International Conference on Information Technology, 5-7, Las Vegas, pgs 608-613 (April 2004), which is incorporated herein by reference as a demonstration of initialization procedures for Hidden Markov Models known by those knowledgeable in the field. A Hidden Markov Model was developed for each of the hand gesture trajectories.

Returning to method 1000, GESTURE MODE ENABLED check process 1001 determines whether the surgeon enabled the gesture recognition mode of operation of system 100. In one aspect, to enable gesture recognition mode, the surgeon depresses a foot pedal on surgeon's console 185 (FIG. 1A). If gesture recognition mode is enabled, check process 1001 transfers to RECEIVE HAND LOCATION DATA process 1010, and otherwise returns thru RETURN 1002.

RECEIVE HAND LOCATION DATA process 1010 receives index finger position and orientation ($p_{index}$, $R_{index}$) and thumb position and orientation ($p_{thumb}$, $R_{thumb}$) for the gesture being made by the surgeon. As noted above, index finger position and orientation ($p_{index}$, $R_{index}$) and thumb position and orientation ($p_{thumb}$, $R_{thumb}$) are based on data from the tracking system. Process 1010 transfers to GENERATE FEATURES PROCESS 1011.

In GENERATE FEATURES process 1011, index finger position and orientation ($p_{index}$, $R_{index}$) and thumb position and orientation ($p_{thumb}$, $R_{thumb}$) are used to generate each of features $f_{1\_o}$ to $f_{n\_o}$ in an observed feature vector $f_{i\_o}$. GENERATE FEATURES process 1011 transfers to COMPARE FEATURE WITH KNOWN POSES process 1012.

COMPARE FEATURE WITH KNOWN POSES process 1012 compares observed feature vector $f_{i\_o}$ with the trained feature set $\{f_i\}$ for each pose. This process determines the likelihood that the observed feature vector is included within a training dataset feature set $\{f_i\}$ for a particular hand gesture pose, i.e., corresponds to the training data set. This can be expressed as $$P(f_{i\_o}|\Omega)$$

where training dataset feature set $\{f_i\}$ is from the object class $\Omega$.

In this example, probability $P(f_{i\_o}|\Omega)$ is:

$$P(f_{i\_o}|\Omega) = \frac{\exp\left[-\frac{1}{2}(f_{i\_o} - \bar{f}_i)^T \sum_{fi}^{-1} (f_{i\_o} - \bar{f}_i)\right]}{(2\pi)^{N/2} |\Sigma_{fi}|^{1/2}}$$

where N is the dimensionality of the feature vector, e.g., n in the above example.

A statistic used to characterize this likelihood is the Mahalanobis distance $d(f_{i\_o})$, which is defined as:

$$d(f_{i\_o}) = \tilde{f}_{i\_o}^T \Sigma_{fi}^{-1} \tilde{f}_{i\_o}$$

where $\tilde{f}_{i\_o} = f_{i\_o} - \bar{f}_i$. The Mahalanobis distance is known to those knowledgeable in the field. See for example, Moghadam, Baback and Pentland, Alex, "*Probabilistic Visual Learning for Object Representation*," IEEE Transactions On Pattern Analysis and Machine Intelligence, Vol. 19, No. 7, pp. 696 to 710 (July 1997), which is incorporated herein by reference.

Using the eigenvectors $\Phi$ and eigenvalues $\Lambda$ of covariance $\Sigma_{fi}$, $\Sigma_{fi}^{-1}$ is used in a diagonalized form so that Mahalanobis distance $d(f_{i\_o})$ is:

$$d(f_{i\_o}) = \tilde{f}_{i\_o}^T [\Phi \Lambda^{-1} \Phi^T] \tilde{f}_{i\_o} = y^T \Lambda^{-1} y$$

where $y = \Phi^T \tilde{f}_{i\_o}$. The diagonalized form allows Mahalanobis distance $d(f_{i\_o})$ to be expressed in terms of the sum:

$$d(f_{i\_o}) = \sum_{j=1}^{N} \frac{y_j^2}{\lambda_j}$$

In this example, this is the expression that is evaluated to determine Mahalanobis distance $d(f_{i\_o})$. Hence, process 1011 generates a Mahalanobis distance $d(f_{i\_o})$. Upon completion, process 1012 transfers to SELECT POSE process 1013.

In SELECT POSE process 1013, the hand gesture pose having the smallest Mahalanobis distance $d(f_{i\_o})$ is selected if Mahalanobis distance $d(f_{i\_o})$ is less than the maximum Mahalanobis distance in the training database for that hand gesture pose. If Mahalanobis distance $d(f_{i\_o})$ is greater than the maximum Mahalanobis distance in the training database for that hand gesture pose, no hand gesture pose is selected. SELECT POSE process 1012 transfers to TEMORAL FILTER PROCESS 1014.

TEMORAL FILTER process 1014 determines whether the result of process 1013 has provided the same result consecutively a predetermined number of times. If process 1013 has provided the same result for the predetermined number of times, TEMPORAL FILTER process 1014 transfers to GESTURE POSE check process 1015, and otherwise returns. The predetermined number of times is selected so that TEMPORAL FILTER process 1014 prevents oscillations or transient detections when switching between hand gesture poses.

GESTURE POSE check process 1015 determines whether the selected hand gesture pose is the hand gesture pose used in a hand gesture trajectory. If the selected hand gesture pose is the hand gesture pose used in a hand gesture trajectory, GESTURE POSE check process 1015 transfers processing to GENERATE VELOCITY SEQUENCE process 1020, and otherwise transfers processing to POSE CHANGE check process 1016.

POSE CHANGE check process 1016 determines whether the hand gesture pose has changed from the last pass through method 1000. If the selected hand gesture pose is the same as the immediately previous temporal filtered gesture pose result, POSE CHANGE check process 1016 returns through RETURN 1003, and otherwise transfers to MAP TO SYSTEM EVENT process 1030.

MAP TO SYSTEM EVENT process 1030 maps the selected hand gesture pose to a system event, e.g., the system event assigned to the hand gesture pose is looked up. Upon finding the system event, MAP TO SYSTEM EVENT process 1030 transfers processing to INJECT SYSTEM EVENT process 1031.

In one aspect, INJECT SYSTEM EVENT process 1031 sends the system event to an event handler in system controller 140 (FIG. 1). In response to the system event, system controller 140 sends an appropriate system command to controllers and/or other apparatus in system 100. For example, if the hand gesture pose is assigned to a turn-on user interface event, system controller 140 sends a command to display controller 150 to turn on the user interface. Display controller 150 executes the part of user interface module 155 on processor 150 needed to turn on the user interface.

When the hand gesture pose is the hand gesture pose used in making a trajectory, processing in method 1000 transfers from GESTURE POSE check process 1015 to GENERATE VELOCITY SEQUENCE process 1020. In one aspect, the principal feature used for hand gesture trajectory recognition is a unit velocity vector. The unit velocity vector is invariant to the starting position of the gesture. In addition, a normalized velocity vector accounts for variations in size or speed of the gesture. Thus, in process 1020, the control point samples are converted into a normalized control point velocity sequence, i.e., into a sequence of unit velocity vectors.

$$v_{cp\_ec}(t) = x_{cp\_ec}(t) - x_{cp\_ec}(t-1) = [\Delta x_{cp\_ec}, \Delta y_{cp\_ec}, \Delta z_{cp\_ec}]'$$

$$u(t) = \frac{v_{cp\_ec}(t)}{|v_{cp\_ec}(t)|} \text{ for } t = 1, 2, \ldots, N-1$$

Upon completion of GENERATE VELOCITY SEQUENCE process 1020, process 1020 transfers processing to CONVERT VELOCITY SEQUENCE INTO SYMBOL SEQUENCE process 1021. As noted above discrete Hidden Markov Model $\Lambda$ requires a sequence of discrete symbols as input. In process 1021, the discrete symbols are generated from the normalized control point velocity sequence through vector quantization.

In one aspect, the vector quantization was performed using a modified K-means clustering with the condition that the process stops when the clustering assignments stop changing. While K-means clustering is used, the process leverages the fact that the features are unit vectors. In this case, vectors, which are similar in direction, are clustered. This is done using the dot-product between each unit feature vector and the normalized cluster center vectors as the similarity metric.

The clustering is initialized with random assignments of vectors to thirty-two clusters and the overall process is iterated multiple times, where the best clustering result is selected based on a maximum total "within" cluster cost metric. Note that in this case, the "within" cluster cost is based on a measure of similarity. Each of the resultant clusters is assigned a unique index, which serves as the symbol for the Hidden Markov Model. An input vector is then mapped to its closest cluster mean and the corresponding index of that cluster is used as the symbol. In this way, a sequence of unit velocity vectors can be translated into a sequence of indices or symbols.

In one aspect, the clustered vectors were assigned a symbol based on a fixed eight-direction two-dimensional vector quantization codebook. Thus, process 1020 generates an observed symbol sequence and transfers to GENERATE GESTURE PROBABILITY process 1023.

In one aspect, to determine which gesture corresponds to the observed symbol sequence, GENERATE GESTURE PROBABILITY process 1023 uses the forward recursion algorithm with the Hidden Markov Models to find a probability that each gesture matches the observed symbol sequence. The forward recursion algorithm is described in Rainer, "*A Tutorial on Hidden Markov Models and Selected Applications in Speech Recognition*," which was previously incorporated herein by reference. Upon completion of GENERATE GESTURE PROBABILITY process 1023, processing transfers to SELECT TRAJECTORY process 1024.

In SELECT TRAJECTORY process 1024, the hand gesture trajectory with the highest probability from among the permissible Hidden Markov Model trajectory gesture models. This probability must also be greater than a given threshold to be accepted. If the highest probability is not greater than the threshold, no hand gesture trajectory is selected. This threshold should be tuned to maximize recognition accuracy while avoiding false recognitions.

Upon completion, SELECT TRAJECTORY process 1024 transfers processing to TRAJECTORY FOUND check process 1025. If SELECT TRAJECTORY process 1024 selected a hand gesture trajectory, TRAJECTORY FOUND check process 1025 transfers processing to MAP TO SYSTEM EVENT process 1030, and otherwise returns through RETURN 1004.

MAP TO SYSTEM EVENT process 1030 maps the selected hand gesture trajectory to a system event, e.g., the system event assigned to the hand gesture trajectory is looked up. Upon finding the system event, MAP TO SYSTEM EVENT process 1030 transfers processing to INJECT SYSTEM EVENT process 1031.

In one aspect, INJECT SYSTEM EVENT process 1031 sends the system event to event handler in system controller 140 (FIG. 1). In response to the system event, system controller 140 sends an appropriate system command to the appropriate controller(s) or apparatus. For example, if the system event is assigned to an action in the user interface, system controller 140 sends a command to display controller 150 to take that action in the user interface, e.g., change the viewing mode of the surgical site.

Process of Presence Detection

Figure 11:
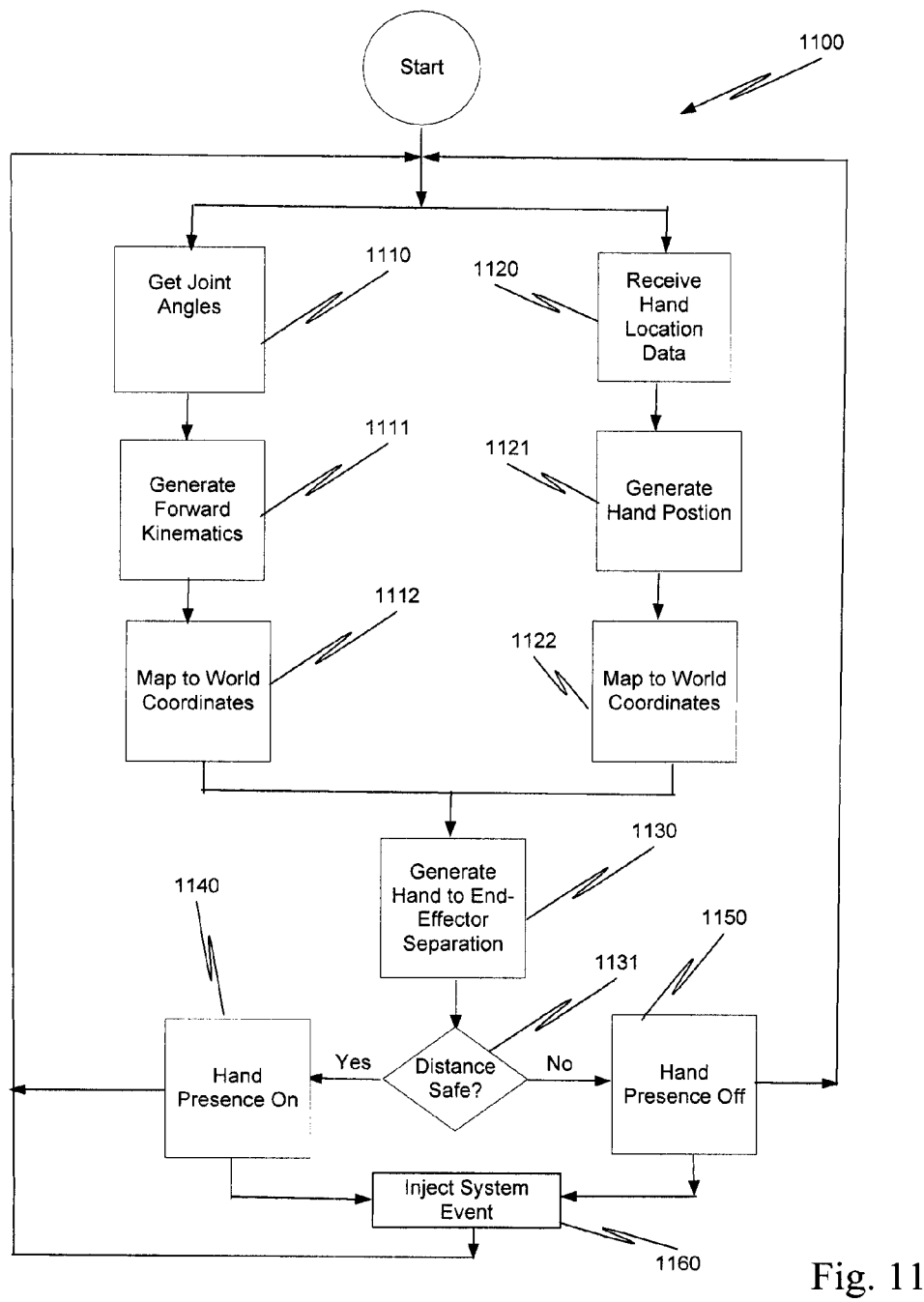
FIG. 11 is a process flow diagram of a process used in the tracking system for hand presence detection.

In yet another aspect, as described above, the tracked position of at least a part of the hand of surgeon 180B is used to determine whether the hand is present on a master manipulator end-effector 621. FIG. 11 is a process flow diagram of one aspect of a process 1100 of presence detection performed, in one aspect, by hand tracking controller 130 in system 100. Process 1100 is performed separately for each of the surgeon's hands in one aspect.

In GET JOINT ANGLES process 1110, the joint angles of master tool manipulator 620 (FIG. 6B) are measured. GET JOINT ANGLES process 1110 transfer processing to GENERATE FORWARD KINEMATICS process 1111.

Since the lengths of the various links in master tool manipulator 620 are known and the position of base 629 of master tool manipulator 620 is known, geometric relationships are used to generate the location of master tool grip 621 in master workspace coordinate system 680. Thus, GENERATE FORWARD KINEMATICS process 1111 generates position $p_{mtm}$ of master tool grip 621 in master workspace coordinate system 680 using the angles from process 1110. GENERATE FORWARD KINEMATICS process 1111 transfers processing to MAP TO WORLD COORDINATES process 1112.

MAP TO WORLD COORDINATES process 1112 maps position $p_{mtm}$ in master workspace coordinate system 680 to a position $p_{mtm\_wc}$ in world coordinate system 670 (FIG. 6A). Specifically, $$p_{mtm\_wc} = {}^{wc}T_{ws} * p_{mtm}$$

where ${}^{wc}T_{ws}$ is a four-by-four homogeneous rigid transformation, which maps coordinates in workspace coordinate system 680 to coordinates in world coordinate system 670.

Upon completion, MAP TO WORLD COORDINATES process 1112 transfers processing to GENERATE HAND TO END EFFCTOR SEPARATION PROCESS 1130.

Returning to RECEIVE HAND LOCATION DATA process 1120, RECEIVE HAND LOCATION DATA process 1120 receives (retrieves) index finger position and orientation ($p_{index}$, $R_{index}$) and thumb position and orientation ($p_{thumb}$, $R_{thumb}$). Index finger position and orientation ($p_{index}$, $R_{index}$) and thumb position and orientation ($p_{thumb}$, $R_{thumb}$) are based on data from the tracking system. RECEIVE HAND LOCATION DATA process 1120 transfers processing to GENERATE HAND POSITION process 1121.

GENERATE HAND POSITION process 1121 maps index finger position and orientation ($p_{index}$, $R_{index}$) and thumb position and orientation ($p_{thumb}$, $R_{thumb}$) to a control point position and orientation in the tracking coordinate system as described above and that description is incorporated herein by reference. Position $P_{hand}$ is the position of the control point in tracking coordinates. GENERATE HAND POSITION process 1121 transfers processing to MAP TO WORLD COORDINATES process 1122.

The use of the control point position in the presence detection is illustrative only and is not intended to be limiting. In view of this disclosure, the presence detection could be done for example, using the position of the tip of the index finger and using the position of the tip of the thumb, or using only one of these positions. The processes described below are equivalent for each of these various positions associated with a part of a human hand.

MAP TO WORLD COORDINATES process 1122 maps position $p_{hand}$ in tracking coordinates to a position $p_{hand\_wc}$ in world coordinate system 670 (FIG. 6A). Specifically, $$P_{hand\_wc} = {}^{wc}T_{tc} * p_{hand}$$

where ${}^{wc}T_{tc}$ is a four-by-four homogeneous rigid transformation, which maps coordinates in tracking coordinate system 650 to coordinates in world coordinate system 670.

Upon completion, MAP TO WORLD COORDINATES process 1122 transfers processing to GENERATE HAND TO END EFFCTOR SEPARATION PROCESS 1130.

GENERATE HAND TO END EFFCTOR SEPARATION PROCESS 1130 generates a separation distance $d_{sep}$ between position $p_{mtm\_wc}$ in world coordinate system 670 and position $p_{hand\_wc}$ in world coordinate system 670. In one aspect separation distance $d_{sep}$ is:

$$d_{sep} = \|p_{mtm\_wc} - p_{hand\_wc}\|$$

Upon completion, GENERATE HAND TO END EFFCTOR SEPARATION PROCESS 1130 transfers processing to DISTANCE SAFE check process 1131.

DISTANCE SAFE check process 1131 compares separation distance $d_{sep}$ to a safe distance threshold. This threshold should be small enough to be conservative while still allowing the surgeon to change grasp or to manipulate the most distal end of the end-effector. If separation distance $d_{sep}$ is less than the safe distance threshold, DISTANCE SAFE check process 1131 transfers to HAND PRESENCE ON process 1140. Conversely, if separation distance $d_{sep}$ is greater than the safe distance threshold DISTANCE SAFE, check process 1131 transfers to HAND PRESENCE OFF process 1150.

HAND PRESENCE ON process 1140 determines whether system 100 is in teleoperation. If system 100 is in teleoperation, no action is required and teleoperation is permitted to continue, and so process 1140 transfers to start process 1100 over. If system 100 is not in teleoperation, HAND PRESENCE ON process 1140 sends a hand present event to INJECT SYSTEM EVENT PROCESS that in turn sends the hand present event to system controller 140.

HAND PRESENCE OFF process 1150 determines whether system 100 is in teleoperation. If system 100 is not in teleoperation, no action is required and so process 1150 transfers to start process 1100 over. If system 100 is in teleoperation, HAND PRESENCE OFF process 1150 sends a hand not present event to INJECT SYSTEM EVENT PROCESS that in turn sends the hand present event to system controller 140.

System controller 140 determines whether the hand present event or the hand not present event requires any change to the system mode of operation and issues an appropriate command. In one aspect, system controller 140 enables teleoperation in response to a hand present event, e.g., permits teleoperation, and disables teleoperation in response to a hand not present event if a teleoperated minimally invasive surgical is coupled to the master tool grip. As is known to those knowledgeable in the field, a teleoperated minimally invasive surgical instrument is couplable to and decoupable from a master tool grip.

In other aspects, the hand present event and hand not present event are used by system controller 140 in combination with other events to determine whether to permit teleoperation. For example, presence detection of the surgeon's head may be combined with presence detection of the surgeon's hand or hands in determining whether to permit tele-operation.

Similarly, as described above, the hand present event and hand not present event are used by system controller 140 to control the display of a user interface on a display of the minimally invasive surgical system. When system controller 140 receives the hand not present event, if the user interface is not turned on, system controller 140 sends a command to display controller 150 to turn on the user interface. Display controller 150 executes the part of user interface module 155 on processor 150 needed to turn on the user interface. When system controller 140 receives the hand present event, if the user interface is turned on, system controller 140 sends a command to display controller 150 to turn off the user interface. Display controller 150 executes the part of user interface module 155 on processor 150 needed to turn off the user interface.

The hand present event and hand not present event can be used by system controller 140 in combination with other events to determine whether to display the user interface. Thus, the user interface display control and the teleoperation control are examples of system mode control using presence detection and are not intended to be limiting to these two specific modes of system control.

For example, the presence detection could be used in control of a proxy visual such as those described more completely below. Also combinations of the various modes, e.g., teleoperation and proxy visual display, could be controlled by system controller 140 based upon the hand present event and hand not present event.

Also, the hand presence detection is useful in eliminating double purposing of master tool grips 621L, 621R, e.g., pushing a foot petal and then using master tool grips 621L, 621R to control a user interface that is displayed in surgeon's console 185B. When the master tool grips are double purposed, e.g., used in control both of a surgical instrument and a user interface, the surgeon typically has to press a foot pedal to switch into the user interface mode of operation. If for some reason, the surgeon fails to depress the foot petal, but believes the system has switched to the user interface mode of operation, movement of the master tool grip can result in unwanted motion of the surgical instrument. Presence detection process 1100 is used to prevent this problem and to eliminate the double purposing of the master tool grips.

With presence detection process 1100, in one example, when the hands presence off event is received by system controller 140, system controller 140 sends a system command to lock master tool manipulators 6201, 620R (FIG. 6A) in place, and sends a system command to display controller 150 to present the user interface on the display of surgeon's console 185B. The motion of the surgeon's hand is tracked and is used to control elements in the user interface, e.g, move a slider switch, change the display, etc. As noted above the control point is mapped into the eye coordinate frame and so can be associated with the location of an element in the user interface. The motion of the control point is used to manipulate that element. This is accomplished without the surgeon having to activate a foot petal and is done so that the surgeon cannot inadvertently move a surgical instrument. Thus, this eliminates the problems associated using the master tool grips to control both the surgical instrument and the user interface.

In the above example, the world coordinate frame is an example of a common coordinate frame. The use of the world coordinate frame as the common coordinate frame is illustrative only and is not intended to be limiting.

Master Finger Tracking Grip

Figure 12:
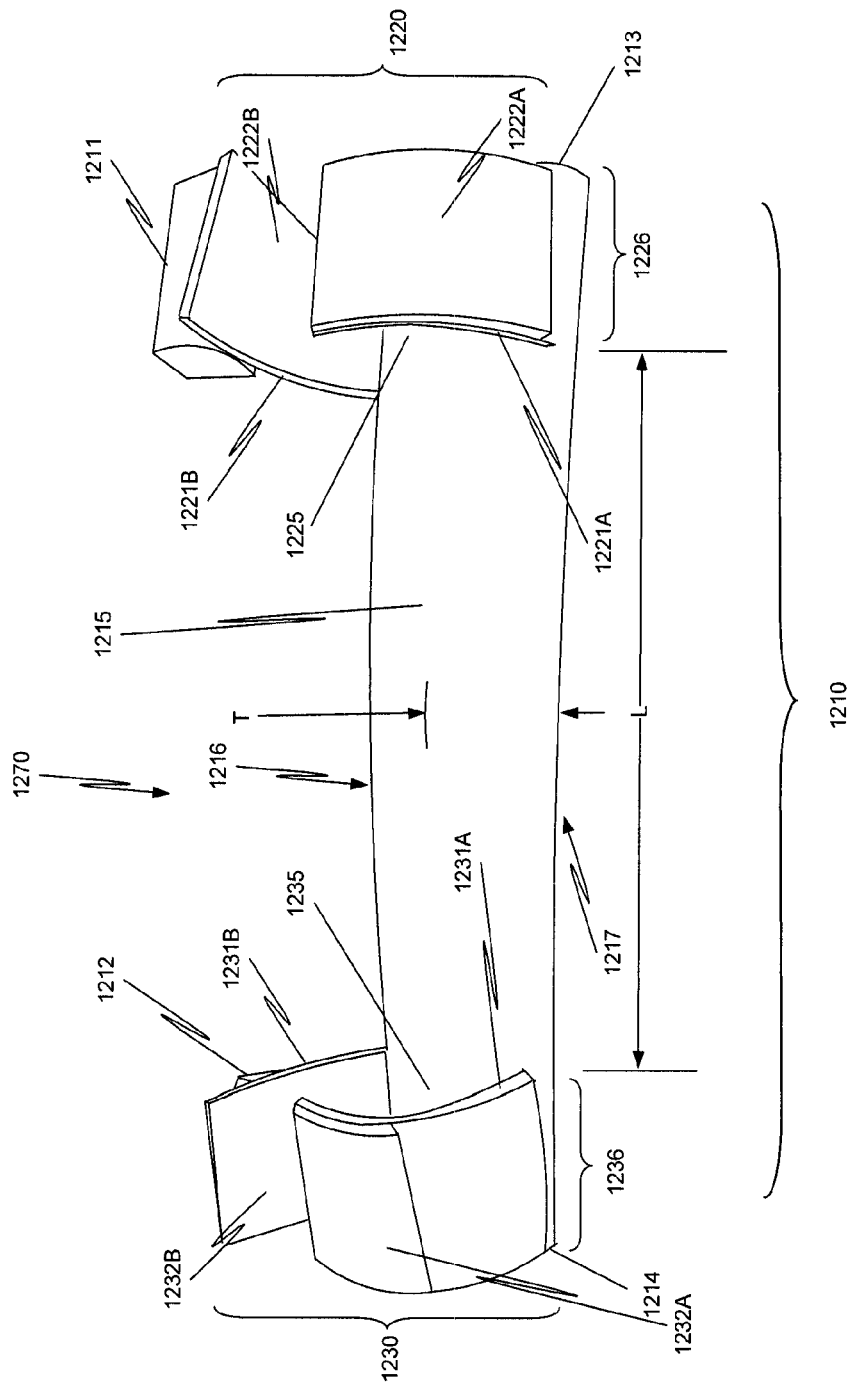
FIG. 12 is an illustration of one example of a master finger tracking device.

FIG. 12 is an illustration of one example of a master finger tracking grip 1270. Master finger tracking grip 1270 is an example of master finger tracking grip 170, 270.

Master finger tracking grip 1270 includes a compressible body 1210 and two finger loops 1220, 1230. Compressible body 1210 has a first end 1213 and a second end 1214. A body section 1215 extends between first end 1213 and second end 1214.

Compressible body 1210 has an outer exterior surface. The outer exterior surface includes a first portion 1216 and a second portion 1217. First portion 1216, e.g., an upper portion, extends between first end 1213 and second end 1214. Second portion 1217, e.g., a bottom portion, extends between first end 1213 and second end 1214. Second portion 1217 is opposite and removed from first portion 1216.

In one aspect, the outer exterior surface is a surface of a fabric casing. The fabric is suitable for use in an operating room. The fabric casing encloses compressible foam. The foam is selected to provide resistance to compression, and expansion as the compression is released. In one aspect, several strips of foam were included within the fabric casing. The foam also must be capable of being bent so that first portion 1216 is positioned between first and second digits of a human hand as the tip of the first digit is moved towards the tip of the second digit.

Body section 1215 has a length L between finger loop 1220 and finger loop 1230. As explained above, length L is selected to limit the separation between a first digit in loop 1220 and a second digit in loop 1230. (See FIG. 2A.)

In one aspect, body section 1215 has a thickness T. As illustrated in FIG. 2C, thickness T is selected so that when master finger tracking grip 1270 is configured such that region 1236 on second portion 1217 of the outer exterior surface adjacent to end 1214 and region 1226 on second portion 1217 adjacent to end 1213 are just touching, second portion 1217 along length L is not in complete contact with itself.

First finger loop 1220 is affixed to compressible body 1210 adjacent to first end 1213. Loop 1220 extends about a region 1225 of first portion 1216 of the outer exterior surface of compressible body 1210. Upon placement of first finger loop 1220 on the first digit of the human hand, region 1225 contacts the first digit e.g., a first part of first portion 1216 of the outer exterior surface contacts the thumb.

In this example, finger loop 1220 has two ends, a first fabric end 1221A and a second fabric end 1221B. End 1221A and end 1221B are ends of a fabric strip that is affixed in body 1210. A piece of loop fabric 1222B is attached to an inner surface of end 1221B, and a piece of hook fabric 1222A is attached to an outer surface of end 1221A. An example of hook fabric and loop fabric is a nylon fastening tape consisting of two strips of nylon fabric, one having tiny hooked threads and the other a coarse surface. The two strips form a strong bond when pressed together. On example of a commercially available fastening tape is VELCRO® fastening tape. (VELCRO® is a registered trademark of Velcro Industries B. V.)

Second finger loop 1230 is affixed to compressible body 1210 adjacent to second end 1214. Loop 1230 extends about a region 1235 of first portion 1216 of the outer exterior surface of compressible body 1210. Upon placement of second finger loop 1230 on the second digit of the human hand, region 1235 contacts the second digit, e.g., a second part of first portion 1216 of the outer exterior surface contacts the index finger. Second part 1235 of first portion is opposite and removed from fist part 1225 of the first portion.

In this example, finger loop 1230 also has two ends, a first fabric end 1231A and a second fabric end 1231B. End 1231A and end 1231B are ends of a fabric strip that is affixed to body 1210. A piece of loop fabric 1232B is attached to an inner surface of end 1231B, and a piece of hook fabric 1232A is attached to an outer surface of end 1231A.

A first location tracking sensor 1211 is affixed to first finger loop 1220. A second location tracking sensor 1212 is affixed to second finger loop 1230. The location tracking sensors can be any of the sensor elements described above. In one example, location tracking sensors 1211, 1212 are passive electromagnetic sensors.

Proxy Visual System

In one aspect, the hand tracking control system is used to control any one of a plurality of proxy visuals that can be used by a surgeon to proctor another surgeon. For example, when surgeon 180 (FIG. 1A) is being proctored by surgeon 181 using master finger tracking grip 170, surgeon 181 uses master finger tracking grip 170 to control a proxy visual of a surgical instrument, while surgeon 180 uses the master tool grip to control a teleoperated slave surgical instrument.

Alternatively, surgeon 181 can telestrate, or can control a virtual hand in the display. Also, surgeon 181 can demonstrate how to manipulate the master tool grip on the surgeon's console by manipulating a virtual image of master tool grip 621 that is presented in the display. These examples of proxy visuals are illustrative only and are not intended to be limiting.

Further, the use of master finger tracking grip 170 while not at a surgeon's console is also illustrative and is not intended to be limiting. For example, with the presence detection system described above, a surgeon at a surgeon's console could move a hand from a master tool grip, and then use that hand to proctor another surgeon as the hand is tracked by the hand tracking system.

To facilitate proctoring, a proxy visual module (not shown) is processed as part of a vision processing subsystem in one aspect. In this aspect, the executing module receives the position and orientation of the control point of the proctor's hand, and renders stereo images, which are composited with the endoscopic camera images in real time and displayed on any combination of surgeon console 185, the assistant display, and patient-side surgeon interface display 187.

When surgeon 181 initiates proctoring by taking a predefined action, e.g., a hand gesture pose, a proxy visual system loop is activated, e.g., the proxy visual module is executed on a processor module. The particular action, e.g., hand gesture pose, used as the predefined action is not essential so long as system controller 140 (FIG. 1) is configured to recognize that action.

Figure 13:
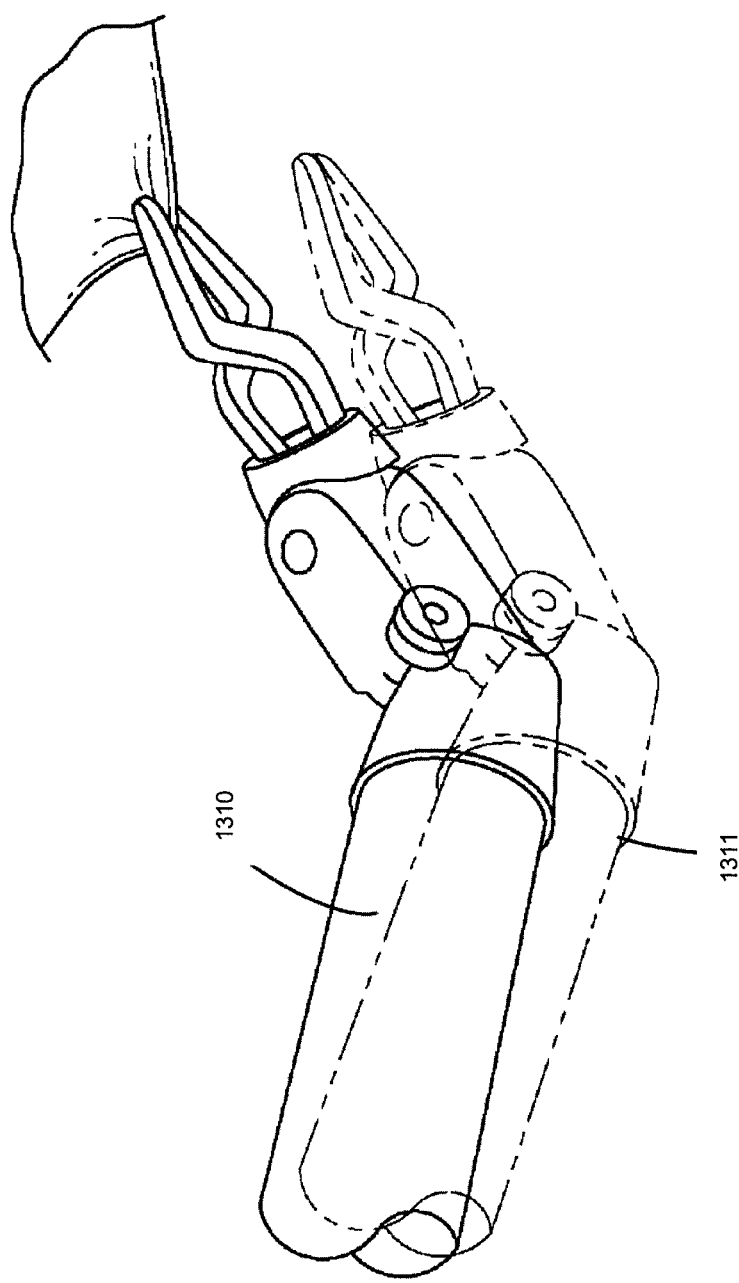
FIG. 13 is an illustration a video image, presented on a display device, including a proxy visual, which in this example includes a virtual ghost instrument, and a teleoperated slave surgical instrument.

In one aspect, the proxy visual is a virtual ghost instrument 1311 (FIG. 13) controlled by master finger tracking grip 170, while teleoperated slave surgical instrument 1310 is controlled by one of the master tool manipulators of surgeon's console 185. Surgeon 181 sees both instruments 1310 and 1311 in display device 187, while surgeon 180 sees both instrument 1310 and 1311 in the stereoscopic display in surgeon's console 185. The use of virtual ghost instrument 1311 as a proxy visual is illustrative only and is not intended to be limiting to this particular image. In view of this disclosure, other images can be used for the proxy visual, which facilitate differentiation between the image representing the proxy visual and the image of the actual end effector of the teleoperated slave surgical instrument.

Virtual ghost instrument 1311 appears similar to actual instrument 1310, except virtual ghost instrument 1311 is displayed in a way that clearly distinguishes virtual ghost instrument 1311 from actual instrument 1310 (e.g., a transparent or translucent ghost-like image, a distinctly colored image, etc.). The control and operation of virtual ghost instrument 1311 is the same as that described above for an actual teleoperated surgical instrument. Thus, surgeon 181 can manipulate virtual ghost instrument 1311 using master finger tracking grip 170 to demonstrate the proper use of teleoperated slave surgical instrument 1310. Surgeon 180 can mimic the motion of virtual ghost instrument 1311 with instrument 1310.

Virtual ghost instruments are described more completely in commonly assigned U.S. Patent Application Publication No. US 2009/0192523 A1 (filed Mar. 31, 2009; disclosing "Synthetic Representation of a Surgical Instrument"), which is incorporated herein by reference in its entirety. See also, U.S. patent application Ser. No. 12/485,503 (filed Jun. 16, 2009, disclosing "Virtual Measurement Tool for Minimally Invasive Surgery"); U.S. patent application Ser. No. 12/485,545 (filed Jun. 16, 2009, disclosing "Virtual Measurement Tool for Minimally Invasive Surgery"); U.S. Patent Application Publication No. US 2009/0036902 A1 (filed Aug. 11, 2008; disclosing "Interactive User Interfaces for Robotic Minimally Invasive Surgical Systems"); U.S. Patent Application Publication No. US 2007/0167702 A1 (filed Dec. 30, 2005; disclosing "Medical Robotic System Providing Three-Dimensional Telestration"); U.S. Patent Application Publication No. US 2007/0156017 A1 (filed Dec. 30, 2005; disclosing "Stereo Telestration for Robotic Surgery") and U.S. Patent Application Publication No. US 2010/0164950 A1

(filed May 13, 2009; disclosing "Efficient 3-D Telestration for Local Robotic Proctoring"), each of which is incorporated herein by reference in its entirety.

Figure 14:
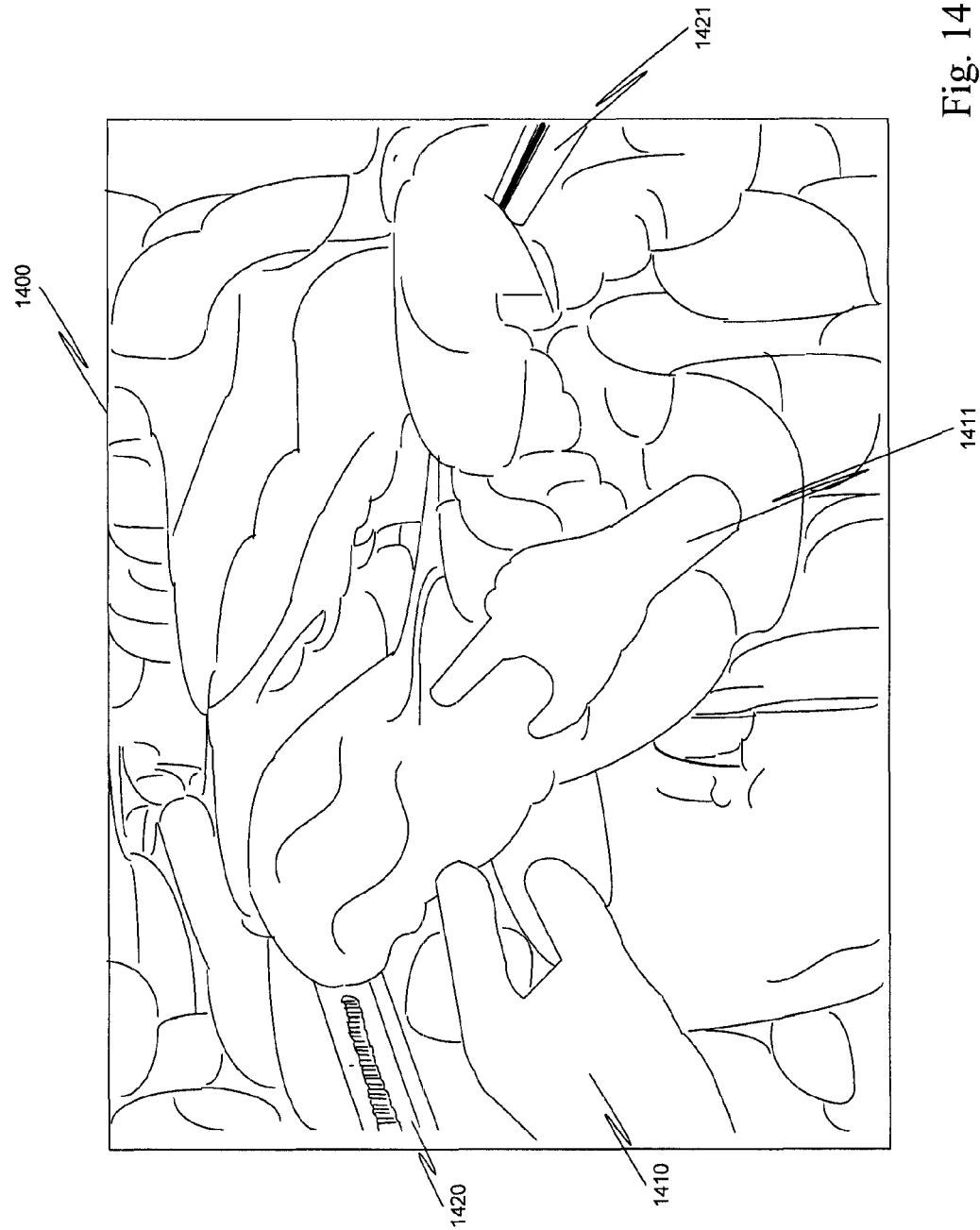
FIG. 14 is an illustration a video image, presented on a display device, including proxy visuals, which in this example includes a pair of virtual hands, and teleoperated slave surgical instruments.

In another aspect, the proxy visual is a pair of virtual hands 1410, 1411 (FIG. 14) controlled by master finger tracking grip 170 and a second master finger tracking grip, which is not visible in FIG. 1. Teleoperated slave surgical instruments 1420, 1421 are controlled by the master tool manipulators of surgeon's console 185. Surgeon 181 sees video image 1400 in display device 187, and surgeon 180 also sees video image 1400 in the stereoscopic display in surgeon's console 185. Virtual hands 1410, 1411 are displayed in a way that clearly distinguishes them from the other objects in video image 1400.

The opening and closing of the thumb and the forefinger of a virtual hand is controlled using grip closure parameter $g_{grip}$, which was described above. The position and orientation of the virtual hand is controlled by the control point position and orientation, as described above, which are mapped into the eye coordinate space, also as described above also.

Thus, as surgeon 181 moves the surgeon's right hand in three dimensions, virtual hand 1411 follows the movement in video image 1400. Surgeon 181 can roll virtual hand 1411 to indicate to surgeon 180 to roll teleoperated slave surgical instrument 1421. Surgeon 181 can move virtual hand 1410 to a particular location and then use thumb and forefinger movement to instruct surgeon 180 to move teleoperated slave surgical instrument 1420 to that location and to grasp the tissue. When surgeon 180 grasps the tissue with instrument 1420, surgeon 181 can use virtual hand 1410 to instruct surgeon 180 how to move the tissue. This all occurs in real time and virtual hands 1410, 1411 are superimposed on the stereoscopic endoscope image. However, the proxy visuals can also be used in a monoscopic system.

Figure 15:
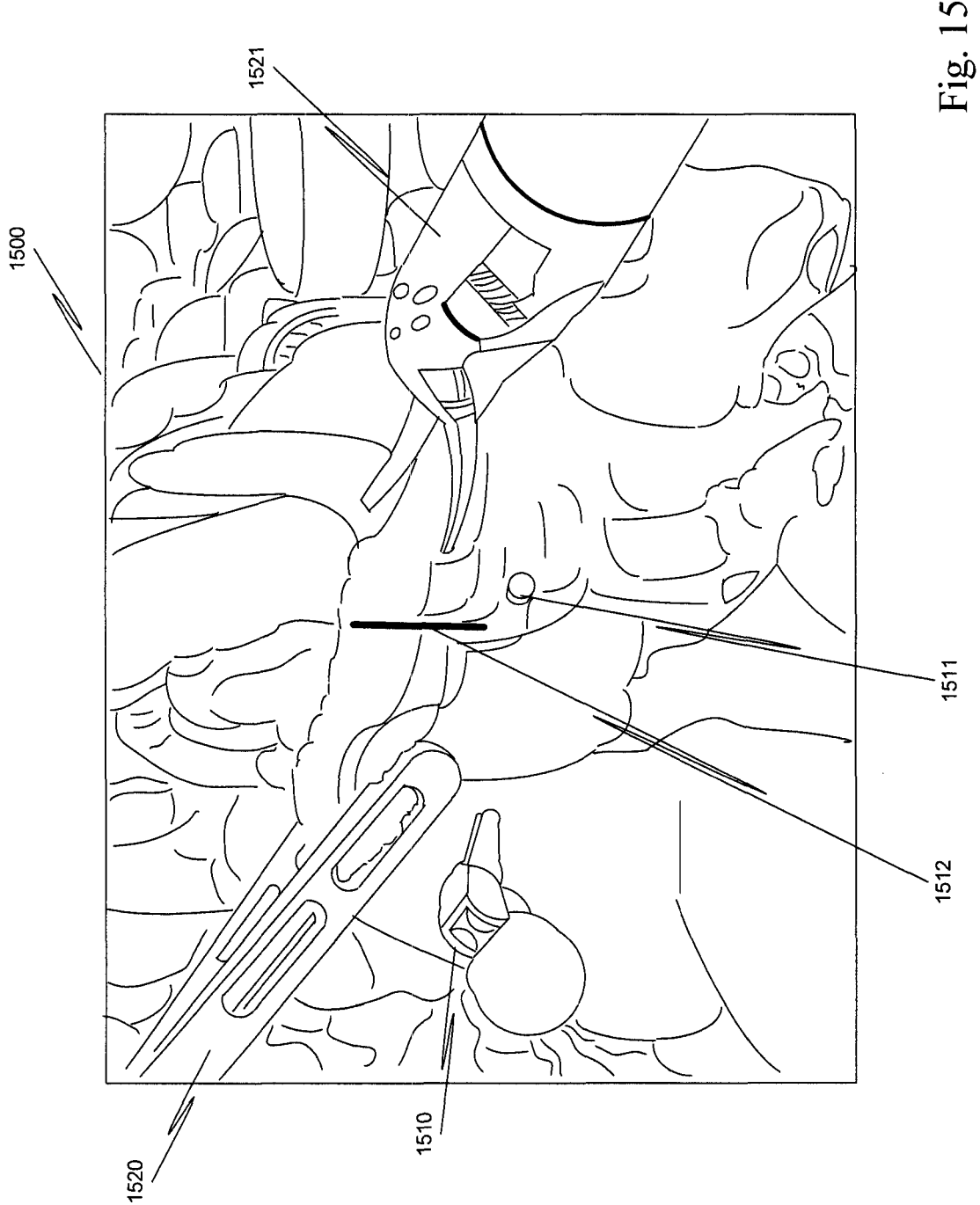
FIG. 15 is an illustration a video image, presented on a display device, including proxy visuals, which in this example includes a virtual telestration device and a virtual ghost instrument, and teleoperated slave surgical instruments.

In another aspect, surgeon 181 changes the display mode using a hand gesture pose so that the proxy visuals are a virtual ghost instrument 1510 and a virtual telestration device 1511, which are presented in video image 1500 (FIG. 15). Telestration device 1511 is controlled by master finger tracking grip 170, while a second master finger tracking grip, which is not visible in FIG. 1, controls virtual ghost instrument 1511.

Teleoperated slave surgical instruments 1520, 1521 are controlled by the master tool manipulators of surgeon's console 185. Surgeon 181 sees video image 1500 in display device 187, and surgeon 180 also sees video image 1500 in the stereoscopic display in surgeon's console 185. Virtual telestration device 1511 and virtual ghost instrument 1411 are displayed in a way that clearly distinguishes them from the other objects in video image 1500.

To telestrate with virtual telestration device 1511, surgeon 181 places the thumb and forefinger together as if grasping an imaginary pen or pencil and then moves the right hand with the thumb and forefinger in this position to telestrate in the displayed video image. In video image 1500, surgeon 181 has so positioned the thumb and forefinger and made mark 1512 to illustrate where the tissue is to be cut using surgical instrument 1521. After mark 1512 was made, surgeon 1810 separated the thumb and forefinger and moved virtual telestration device 1511 to the position shown in video image 1500.

The marking capability of virtual telestration device 1511 is controlled using grip closure parameter $g_{grip}$, which was described above. As noted above, when the thumb and forefinger are just touching, the grip closure parameter $g_{grip}$ is mapped to an initial value in a second range, and so when grip closure parameter $g_{grip}$ is in the second range, telestration is enabled for telestration device 1511. The control point position and orientation after being mapped to the eye coordinate system is used to control the motion of virtual telestration device 1511.

The above description and the accompanying drawings that illustrate aspects and embodiments of the present inventions should not be taken as limiting—the claims define the protected inventions. Various mechanical, compositional, structural, electrical, and operational changes may be made without departing from the spirit and scope of this description and the claims. In some instances, well-known circuits, structures, and techniques have not been shown or described in detail to avoid obscuring the invention.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of the device in use or operation in addition to the position and orientation shown in the figures. For example, if the device in the figures is turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations) and the spatially relative descriptors used herein interpreted accordingly. Likewise, descriptions of movement along and around various axes include various special device positions and orientations.

The singular forms "a", "an", and "the" are intended to include the plural forms as well, unless the context indicates otherwise. The terms "comprises", "comprising", "includes", and the like specify the presence of stated features, steps, operations, processes elements, and/or components but do not preclude the presence or addition of one or more other features, steps, operations, processes elements, components, and/or groups. Components described as coupled may be electrically or mechanically directly coupled, or they may be indirectly coupled via one or more intermediate components.

Memory refers to a volatile memory, a non-volatile memory, or any combination of the two. A processor is coupled to a memory containing instructions executed by the processor. This could be accomplished within a computer system, or alternatively via a connection to another computer via modems and analog lines, or digital interfaces and a digital carrier line.

Herein, a computer program product includes a medium configured to store computer readable code needed for any one or any combination of the processes described with respect to hand tracking or in which computer readable code for any one or any combination of processes described with respect to hand tracking is stored. Some examples of computer program products are CD-ROM discs, DVD discs, flash memory, ROM cards, floppy discs, magnetic tapes, computer hard drives, servers on a network and signals transmitted over a network representing computer readable program code. A non-transitory tangible computer program product includes a non-transitory tangible medium configured to store computer readable instructions for any one of, or any combination of processes described with respect to various controllers or in which computer readable instructions for any one of, or any combination of processes described with respect to the various controllers are stored. Non-transitory tangible computer program products are CD-ROM discs, DVD discs, flash memory, ROM cards, floppy discs, magnetic tapes, computer hard drives and other non-transitory physical storage mediums.

In view of this disclosure, instructions used in any one of, or any combination of processes described with respect to hand tracking can be implemented in a wide variety of computer system configurations using an operating system and computer programming language of interest to the user.

The use of different memories and processors in FIG. 1 is illustrative only and is not intended to be limiting. In some aspects, a single hardware processor could be used and other aspects multiple processors could be used.

Also, for each of illustration, the various processes were distributed between a hand tracking controller and a system controller. This also is illustrative and is not intended to limiting. The various processes can be distributed across controllers or consolidated in a controller without changing the principles of operation in the hand tracking process.

All examples and illustrative references are non-limiting and should not be used to limit the claims to specific implementations and embodiments described herein and their equivalents. The headings are solely for formatting and should not be used to limit the subject matter in any way, because text under one heading may cross reference or apply to text under one or more headings. Finally, in view of this disclosure, particular features described in relation to one aspect or embodiment may be applied to other disclosed aspects or embodiments of the invention, even though not specifically shown in the drawings or described in the text.

We claim:

1. A surgical system comprising:
a master finger tracking device further comprising:
 a first finger loop;
 a first sensor element, wherein an output of the first sensor element comprises a first signal used in control of a slave device of the surgical system;
 a second finger loop;
 a second sensor element, wherein an output of the second sensor element comprises a second signal used in the control of the slave device of the surgical system; and
 a compressible body comprising a first end and a second end opposite the first end,
 wherein the first finger loop is affixed adjacent to the first end, and wherein the second finger loop is affixed adjacent to the second end;
 wherein upon placement of the first finger loop on a first digit of a human hand and the second finger loop on a second digit of the human hand, the first sensor element is positioned adjacent to the first digit of the human hand, the second sensor element is positioned adjacent to the second digit of the human hand, and the compressible body is positioned between the first and second digits so that the compressible body provides resistance to movement of the first digit towards the second digit.

2. The system of claim 1, wherein the compressible body comprises:
an outer exterior surface including a first portion extending between the first and second ends, and a second portion, opposite from the first portion, extending between the first and second ends.

3. The system of claim 2,
wherein the first finger loop affixed to the compressible body adjacent to the first end extends about the first portion of the outer exterior surface,
wherein upon placement of the first finger loop on the first digit of the human hand, a first part of the first portion of the outer exterior surface contacts the first digit,
wherein the second finger loop affixed to the compressible body adjacent to the second end extends about the first portion of the outer exterior surface, and
wherein upon placement of the second finger loop on the second digit of the human hand, a second part of the first portion of the outer exterior surface contacts the second digit of the human hand.

4. The system of claim 1, wherein a length of the compressible body is selected to limit a separation between the first digit of the human hand and the second digit of the human hand following the placement of the first finger loop on the first digit of the human hand and the second finger loop on the second digit of the human hand.

5. The system of claim 1, wherein a thickness of the compressible body is selected so that upon a tip of the first digit of the human hand placed in the first finger loop just touching a tip of the second digit of the human hand placed in the second finger loop, the compressible body is less than fully compressed.

6. The system of claim 1, further comprising a teleoperated slave surgical instrument having an end effector, wherein the compressible body provides haptic feedback corresponding to a grip force of the end effector.

7. The system of claim 1, wherein a portion of each of the first and second finger loops comprises a hook fabric and another portion of each of the first and second finger loops comprises a loop fabric, and wherein the loop fabric removably attaches to the hoop fabric to form a closed finger loop.

8. The system of claim 1, wherein each of the first and second sensor elements comprises a passive electromagnetic sensor.

9. The system of claim 8, wherein each of the passive electromagnetic sensors has six degrees of freedom.

10. A method of operating a surgical system comprising:
receiving, by a controller in the surgical system, first sensed data representing N degrees of freedom of a first digit of a human hand and second sensed data representing N degrees of freedom of a second digit of the human hand, where N is a positive non-zero integer number;
mapping, by the controller, the first sensed data and the second sensed data to a control point location,
 wherein the control point has six degrees of freedom, and
 wherein the six degrees of freedom are less than or equal to 2*N degrees of freedom;
mapping, by the controller, the first sensed data and the second sensed data to a parameter having a single degree of freedom; and
generating, by the controller, a system command in the surgical system, wherein the system command is based on the control point location and the parameter.

11. The method of claim 10, wherein the parameter comprises a grip closure distance.

12. The method of claim 10, wherein the parameter comprises an orientation.

13. The method of claim 12, wherein the orientation comprises yaw.

14. The method of claim 10, wherein N is six.

15. The method of claim 10, wherein N is five.

16. A method of operating a surgical system comprising:
receiving, by a controller in the surgical system, first sensed data representing three degrees of freedom of a first digit of a human hand and second sensed data representing three degrees of freedom of a second digit of the human hand;

mapping, by the controller, the first sensed data and the second sensed data to a control point position, wherein the control point has three degrees of freedom;

mapping, by the controller, the first sensed data and the second sensed data to a parameter having a single degree of freedom; and generating, by the controller, a system command, based on the control point location and the parameter, for a slave surgical instrument that does not include a wrist mechanism in the surgical system.

17. The method of claim 16, wherein the parameter comprises a grip closure distance.

18. The method of claim 16, wherein the parameter comprises roll.

* * * * *